US010126309B2

(12) United States Patent
Wiktorowicz

(10) Patent No.: US 10,126,309 B2
(45) Date of Patent: Nov. 13, 2018

(54) METHOD FOR THE DETECTION OF AN ALBUMIN ISOFORM

(71) Applicant: THE BOARD OF REGENTS OF THE UNIVERSITY OF TEXAS SYSTEM, Austin, TX (US)

(72) Inventor: John E. Wiktorowicz, League City, TX (US)

(73) Assignee: THE BOARD OF REGENTS OF THE UNIVERSITY OF TEXAS SYSTEMS, Austin, TX (US)

( * ) Notice: Subject to any disclaimer, the term of this patent is extended or adjusted under 35 U.S.C. 154(b) by 74 days.

(21) Appl. No.: 14/799,778

(22) Filed: Jul. 15, 2015

(65) Prior Publication Data

US 2015/0316562 A1 Nov. 5, 2015

Related U.S. Application Data

(63) Continuation of application No. 13/490,360, filed on Jun. 6, 2012, now Pat. No. 9,103,826.

(60) Provisional application No. 61/493,923, filed on Jun. 6, 2011.

(51) Int. Cl.
*G01N 33/68* (2006.01)
*G01N 33/564* (2006.01)
*G01N 33/569* (2006.01)

(52) U.S. Cl.
CPC ....... *G01N 33/6869* (2013.01); *G01N 33/564* (2013.01); *G01N 33/56983* (2013.01); *G01N 33/6851* (2013.01); *G01N 2333/185* (2013.01); *G01N 2333/47* (2013.01); *G01N 2333/4716* (2013.01); *G01N 2333/5428* (2013.01); *G01N 2333/55* (2013.01); *G01N 2333/76* (2013.01); *G01N 2800/26* (2013.01)

(58) Field of Classification Search
CPC ........... G01N 33/6851; G01N 2333/47; G01N 2333/76; G01N 2333/765
See application file for complete search history.

(56) References Cited

U.S. PATENT DOCUMENTS

2013/0236917 A1\* 9/2013 Van Eyk ............ G01N 33/6893 435/7.92

FOREIGN PATENT DOCUMENTS

WO WO/10/043973 4/2010
WO WO/12/170556 12/2012

OTHER PUBLICATIONS

Jacobs et al. "Utilizing Human Blood Plasma for Proteomic Biomarker Discovery" (2005) Journal of Proteome Research, vol. 4: 1073-1085.\*

Matsuura et al. "Multielement Determination and Speciation of Major-to-trace Elements in Black Tea Leaves by ICP-AES and ICP-MS with the aid of Size Exclusion Chromatography" (2001), Analystical Sciences, vol. 17: 391-398.\*
Pretzer et al. "Saturation fluorescence labeling of proteins for proteomic analyses" (2008), Analytical Biochemistry, vol. 374: 250-262.\*
Stanton et al. "Gel Filtration Chromatography" (2004) Methods in Molecular Biology: HPLC of Peptides and Proteins, vol. 251: 55-73.\*
Barnidge et al. Absolute Quantification of the Model Biomarker Prostate-Specific Antigen in Serum by LC-MS/MS Using Protein Clevage and Isotope Dilution Mass Spectrometry, (2004), Journal of Proteome Research, vol. 3: 644-652.\*
Bechtold et al. "Biological markers of exposure to benzene: S-phenylcysteine in albumin" (1992) Carcinogenesis, vol. 13, No. 7: 1217-1220. (Year: 1992).\*
Read et al. "Biomarkers of organophosphorus nerve agent exposure: comparison of phosphorylated butyrylcholinesterase and phosphylated albumin after oxime therapy" (Oct. 2009), Arch Toxicol, vol. 84: 25-36. (Year: 2009).\*
Sahab et al. "Methodology and Application of Disease Biomarker Identificatin in Human Serum" (2007), Biomarker Insight, vol. 2: 21-43. (Year: 2007).\*
Williams et al. "Posphylated tyrosine in albumin as a biomarker of exposure to organophosphorus nerve agents" (Mar. 2007), Arch Toxicol, vol. 81:627-639. (Year: 2007).\*
Zhou et al. "An investigation into the human serum 'interactome'" (2004) Electrophoresis, vol. 25: 1289-1298. (Year: 2004).\*
Albuquerque, et al., 2009. Two-Dimensional D Difference Gel Electrophoresis (DiGE) Analysis of Plasmas from Dengue Fever Patients. J. Proteome Res. 8:5431-5441.
Bozza, F., Cruz,O., Zagne,S., Azeredo,E., Nogueira,R., Assis,E., Bozza,P and Kubelka,C. 2008. Multiplex cytokine profile from dengue patients: MIP-1beta and IFN-gamma D as predictive factors for severity. BMC Infectious Diseases 8:86.
Brasier et al., 2010. Discovery proteomics and nonparametric modeling pipeline in development of a candidate biomarder panel for dengue hemorrhagic fever. Clinical and Translational Science 5(1 ): 8-20.
Brasier et al., 2012. A three-component biomarker panel for prediction of dengue hemorrhagic fever. Am. J. Trop. Med. Hyg. 86(2): 341-348.
Chareonsirisuthigul,T., Kalayanarooj,S., and Uboi,S. 2007. Dengue virus (DENV) antibody-dependent enhancement of infection upregulates the production of anti-inflammatory cytokines, but suppresses anti-DENV free radical and pro-inflammatory cytokine production, in THP-1 cells. J. Gen. Virol. 88:365-375.
Chaturvedi et al. Cytokine cascade in dengue hemorrhagic fever: implications for pathogenesis. FEMS Immunology and Medical Microbiology, 2000, No. 28, pp. 183-188, p. 185, col2.
Cook et al. Tree and spline based association analysis of gene-gene interaction models for ischemic stroke. Stat. Med. 23, 1439-1453 (2004).
Dowsey, A.W., Morris,J.S., Gutstein,H.B., and Yang,G.Z. 2010. Informatics and statistics for analyzing 2-d gel electrophoresis images. Methods Mol. Bioi 604:239-255.

(Continued)

*Primary Examiner* — Teresa E Knight

(74) *Attorney, Agent, or Firm* — Norton Rose Fulbright US LLP

(57) ABSTRACT

The present invention provides methods for detecting, analyzing, and identifying biomolecules used to identifying patient with dengue-like symptom who are at risk of DHF. The inventive method comprises detecting in a sample from a subject dengue infected patient one or more biomarkers selected from the group consisting of IL-10, fibrinogen, C4A, immunoglobulin, tropomyosin, and three isoforms of albumin, and which are used in a predictive MARS model to detect patients with risk of developing DHF.

5 Claims, 24 Drawing Sheets

(56) References Cited

OTHER PUBLICATIONS

Figure 1A:
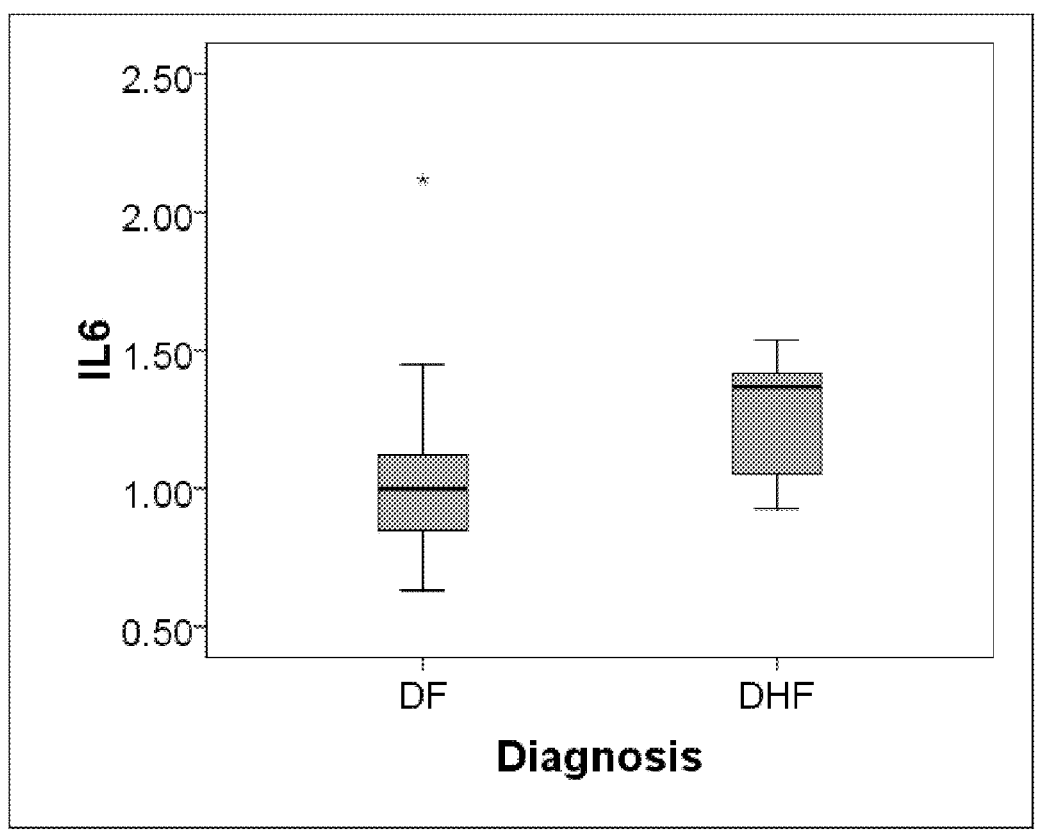

Endy,T.P., Nisalak,A., Chunsuttitwat,S., Vaughn,D.W., Green,S., Ennis,F.A., Rothman,A.L., and Libraty,D.H. 2004. Relationship of Preexisting Dengue Virus (DV) Neutralizing Antibody Levels to Viremia and Severity of Disease in a Prospective Cohort Study of DV Infection in Thailand. J Infect Dis 189:990-1000.
Fawcett. 2006. An introduction to ROC analysis. Pattern Recognition Letters 27:861-874.
Friedman,J. H. 1991. Multivariate Adaptive Regression Splines. Annals of Statistics 19:1-67.
Gilbert. Dissertation. In Search of Novel Dengue Biomarkers Using SELDI-TOF MS and Other Proteomic Technologies. A thesis submitted in partial fulfillment of the requirements for the degree of Master of Science in Experimental Medicine in the University of McGill University, Sep. 2010.
Graham,R.R., Juffrie,M., Tan,R., Hayes,C.G., Laksono,l., Ma'roef,C., Erlin, Sutaryo, Porter,K.R., and Halstead,S.B. 1999. A prospective seroepidemiologic study on dengue in children four to nine years of age in Yogyakarta, Indonesia I. studies in 1995-1996. Am J Trap Med Hyg 61:412-419.
Green, S., A. Rothman. Immunopathological mechanisms in dengue and dengue hemorrhagic fever. Curr. Opin. lnfec. Dis. 19,429-436 (2006).
Guzman, M., G. Kouri. Dengue: an update. Lancet Infect Dis. 2(1), 33-42 (2002).
Guzman,M.G., Kouri,G., Bravo,J., Valdes,L., Vazquez,S., and Halstead,S.B. 2002. Effect of age on outcome of secondary dengue 2 infections. Int. J Infect. Dis 6:118-124.
International Search Report, PCT/US2012/0411131, dated Aug. 27, 2012.
Jamaluddin,M., Wiktorowicz,J.E., Soman,K.V., Boldogh,l., Forbus,J., Spratt,H., Garofalo,R.P., and Brasier,A.R. 2010. Role of Peroxiredoxin-1 and -4 in Protection of RSV-induced Cysteinyl-oxidation of Nuclear Cytoskeletal Proteins. J Viral 84:9533-9545.
Karp, Feret,R., Rubtsov,D.V., and Lilley,K.S. 2008. Comparison of DIGE and post-stained gel electrophoresis with both traditional and SameSpots analysis for quantitative proteomics. Proteomics 8:948-960.
Kliks et al. Antibody-dependent enhancement of dengue virus growth in human monocytes as a risk factor for dengue hemorrhagic fever. Am. J. Trap. Med. Hyg. 40(4), 444-51 (1989).
Martina,B.E.E., Koraka,P., and Osterhaus,A.D.M.E. 2009. Dengue Virus Pathogenesis: an Integrated View. Clin. Microbial. Rev. 22:564-581.
Miseta., and Csutora,P. 2000. Relationship between the occurrence of cysteine in proteins and the complexity of organisms. Molecular Biology of Evolution 17{8}:1232-1239.
Nascimento et al. Alternative Complement Pathway Deregulation is Correlated with Dengue Severity. PLoS One, 2009, vol. 4 {8}.
Nasirudeen et al. Gene Expression Profiling by Microarray Analysis Reveals an Important Role for Caspase-1 in Dengue Virus-Induced p53-Mediated Apoptosis. Journal of Medical Virology {2009) 81: 1069-1081.
Oishi et al. Correlation between increased platelet-associated lgG and thrombocytopenia in secondary dengue virus infections. J. Med. Virol. 71, 259-64 (2003).
Perez,A.B., Garcia,G., Sierra,B., Alvarez,M., Vazquez,S., Cabrera,M.V.,Rodriguez,R., Rosario,D., Martinez,E., Denny,T. et al2004. IL-10 levels in Dengue patients: some findings from the exceptional epidemiological conditions in Cuba. J Med Virol 73:230-234.
Pretzer, E.P., and Wiktorowicz,J.E. 2008. Saturation fluorescence labeling of proteins for proteomic analyses. Anal. Biochem. 374:250-262.
Rifai, N., and Gerszten,R.E. 2006. Biomarker Discovery and Validation. Clinical Chern is try 52:1635-1637.
Srichaikul,T., Nimmanitaya,S., Artchararit,N., Siriasawakui,T., and Sungpeuk,P. 1977. Fibrinogen Metabolism and Disseminated Intravascular Coagulation in Dengue Hemorrhagic Fever. Am J Trop Med Hyg 26:525-532.
Stephenson, J. R. Understanding dengue pathogenesis: implications for vaccine design. Bulletin of World Health Organization 83, 308-14 (2005).
Thayan,R., Huat,T.L., See,L.L., Tan,C.P., Khairullah,N.S., Yusof,R., and Devi,S. 2009. The use of two-dimension electrophoresis to identify serum biomarkers from patients with dengue haemorrhagic fever. Trans. R. Soc. Trop Med Hyg 103:413-419.
Thomas,L., Verlaeten,O., Cabie,A., Kaidomar,S., Moravie,V., Martiai,J., Najioullah,F., Plumelle,Y., Fonteau,C., Dussart,P. et al 2008. Influence of the dengue serotype, previous dengue infection, and plasma viral load on clinical presentation and outcome during a dengue-2 and dengue-4 co-epidemic. Am J Trop Med Hyg 78:990-998.
Villar-Centeno, L.A., Diaz-Quijano,F.A., and Martinez-Vega,R.A. 2008. Biochemical Alterations as Markers of Dengue Hemorrhagic Fever. Am J Trop Med Hyg 78:370-374.
Wills et al. "Coagulation Abnormalities in Dengue Hemorrhagic Fever: Serial Investigations in 167 Vietnamese Children with Dengue Shock Syndrome." (2002) Clinical Infectious Diseases, vol. 35: 277-285.
World Health Organization, Dengue Hemorrhagic Fever: Diagnosis, Treatment, Prevention, and Control. (1997) World Health Organization: 24-33.
York et al. "Multivariate adaptive regression splines: a powerful method for detecting disease-risk relationship differences among subgroups." (2006) Statistics in Medicine, vol. 25: 1355-1367.
Zhang,W., and Chait,B.T. 2000. ProFound: An Expert System for Protein Identification Using Mass Spectrometric Peptide Mapping Information. Anal. Chem. 72:2482-2489.

* cited by examiner

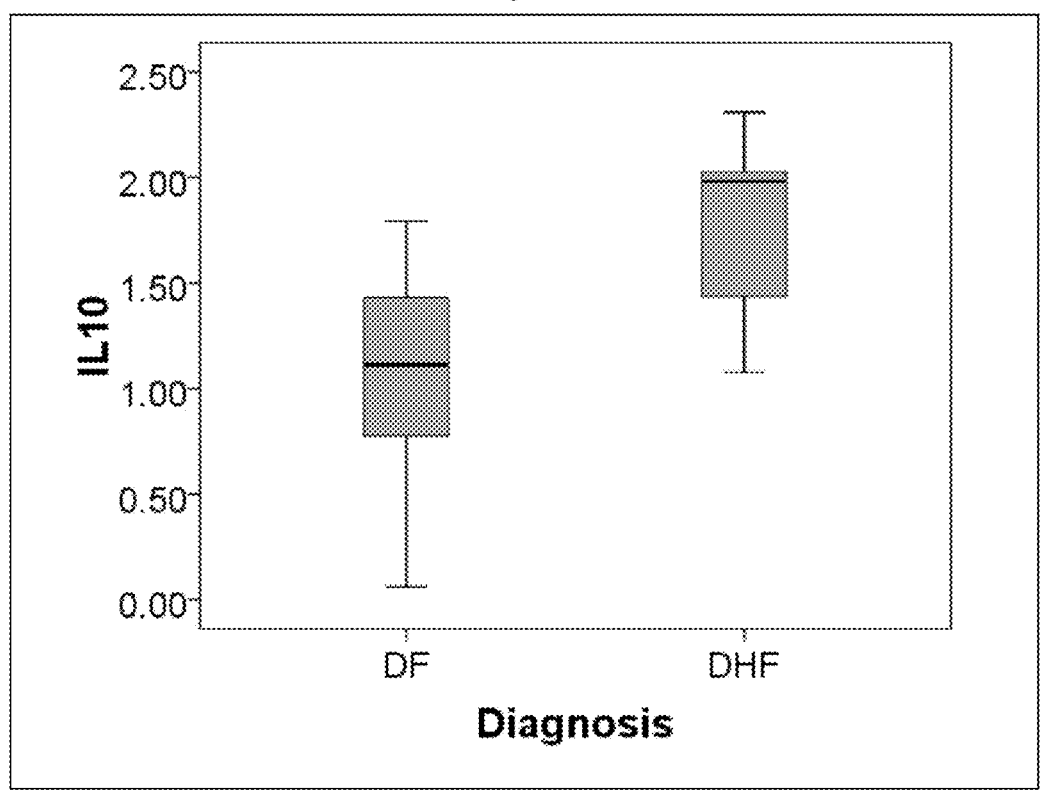

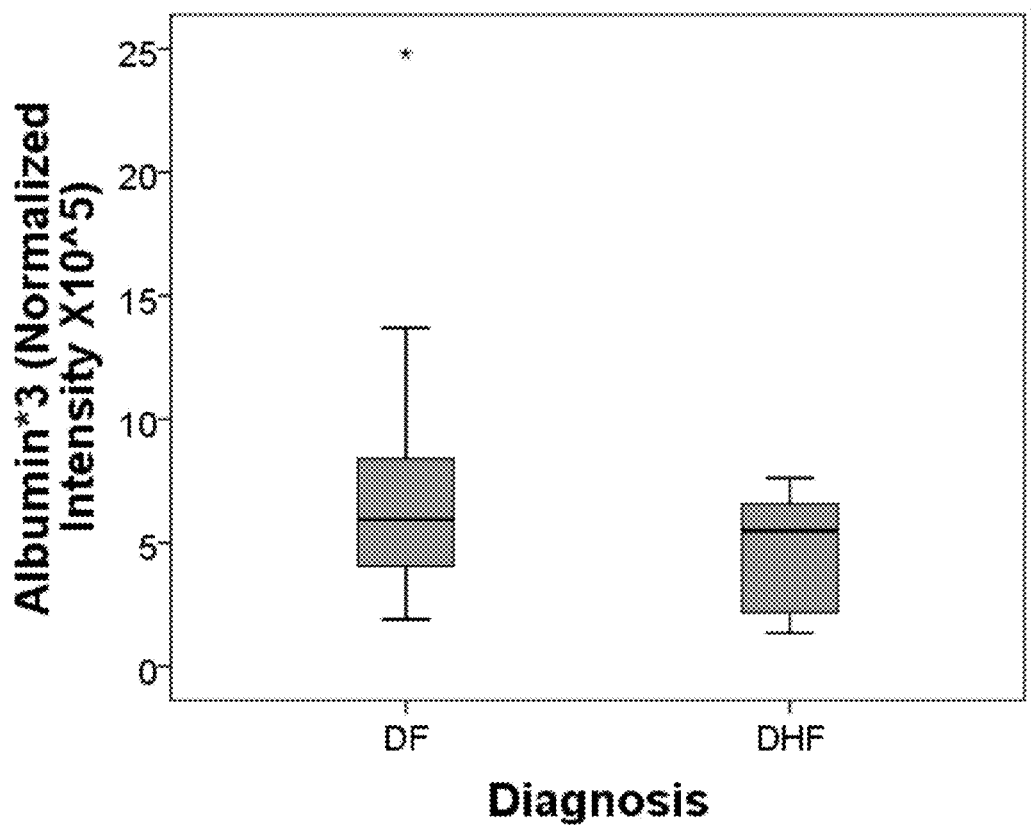

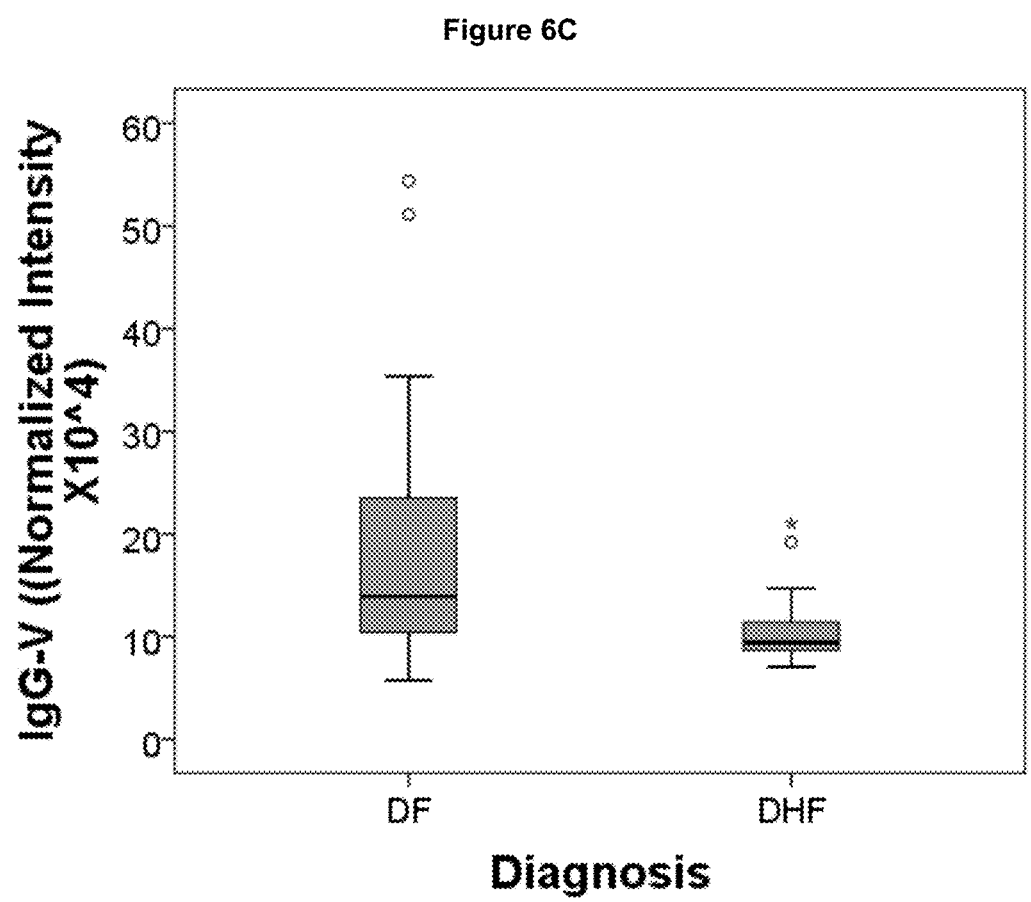

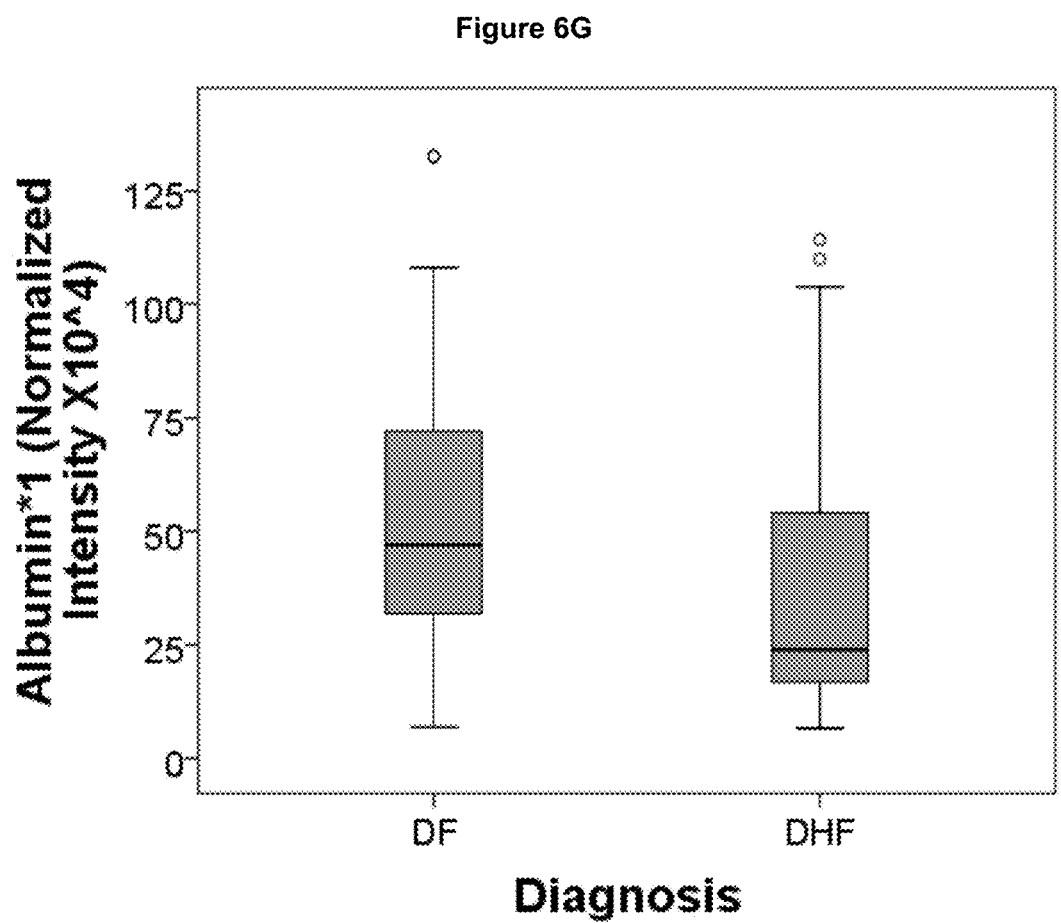

METHOD FOR THE DETECTION OF AN ALBUMIN ISOFORM

CROSS-REFERENCE TO RELATED APPLICATION

The present application is a continuation of U.S. patent application Ser. No. 13/490,360, filed Jun. 6, 2012, which claims the benefit of priority to U.S. Provisional Patent Application Ser. No. 61/493,923 filed on Jun. 6, 2011, both of which are hereby incorporated by reference in their entirety.

BACKGROUND OF THE INVENTION

Dengue remains an international public health problem affecting urban populations in tropical and sub-tropical regions, where it is currently estimated that about 2.5 billion people are at risk of dengue infection. Dengue virus is a single positive-stranded RNA virus of the family Flaviviridae; genus *Flavivirus*, which is transmitted among humans primarily by *Aedes aegypti* mosquitoes. In humans, dengue infection can produce diseases of a wide spectrum of severity, from asymptomatic to flu-like dengue fever (DF), to life-threatening dengue hemorrhagic fever (DHF), or dengue shock syndrome (DSS). DHF is particularly associated with capillary leakage, hemorrhage, circulatory shock, and representing life-threatening complication.

Due to a number of factors, including increasing urbanization and globalization of travel, dengue disease is re-emerging in the Americas, where it has caused an estimated 890,000 cases, of which 26,000 were DHF (45). The mortality of DHF is age-dependent, primarily occurring in the children and the elderly (3, 45). In Southeast Asia, a disproportionate amount of DHF hospitalizations are of children whereas in the Americas, there is a more even distribution across ages.

The risk factors and etiology of DHF are not fully understood. There are four serotypes of dengue virus, and often a region may have more than one circulating serotype at a time. Many epidemiological studies have found an 40 to 80-fold increased risk of DHF after a second infection with a different serotype (3, 5,6). This observation has led to the "antibody dependent enhancement theory," which hypothesizes that neutralizing antibodies generated during the adaptive immune response cross-react, but do not neutralize, a second infecting dengue virus serotype. These antibody-viral complexes are taken up by immunocytes by binding the cell-surface Fc receptors. As a result, highly activated immunocytes release enhanced cytokines and factors involved in vascular leakage. Other evidence points to DHF being the result of an interplay between host and viral factors, including cell-mediated immunity (1).

Currently, there is no drug therapy or vaccine for DHF. However, early therapy aiming to treat individual symptoms can reduce mortality. Typical dengue treatments include transfusion of fresh blood or platelets to correct blooding, giving intravenous (IV) fluids and electrolytes to correct electrolyte imbalances and dehydration, and oxygen therapy to treat low blood oxygen. Although DHF fatality rates can exceed 20%, early identification and intensive supportive therapy can reduce the rate to less than 1% (7). Therefore, detection and differentiation of dengue disease severity early in the course of infection is critical for the prognosis and treatment of patients.

Currently diagnosis of dengue virus infection is made by physical examination of the patient and routine clinical laboratory tests such as complete blood count (CBC). A positive tourniquet test has been considered to be a sensitive parameter for dengue diagnosis. More than 90% of cases can be correctly diagnosed for dengue infection by taking into account of the patient's medical history, physical signs, and a positive tourniquet test. However, a definitive diagnosis for dengue infection requires laboratory confirmation, especially in regions where other endemic infectious diseases mimic the syndromes caused by dengue infection. Definitive diagnostic tests for dengue infection include isolation of viable virus, and identification of viral RNA in serum or plasma. Several factors limit routine application of these tests, including the timing of specimen collection, and the availability of equipment.

Serological techniques are also used in dengue diagnosis. Serological tests are commonly used in the field because timing of specimen collection is flexible, and immunoglobulins are not easily degraded or inactivated by harsh treatment of specimens. The most commonly used serological techniques for the diagnosis of dengue infection are the hemagglutination inhibition (HI) test, and immunoglobulin M or G (IgM or IgG) captured enzyme-linked immunosorbent assay (ELISA). Results from both IgM and IgG captured ELISA can be used to differentiate between the cases of primary and secondary dengue infection. In primary infection, the ratio of anti-dengue IgM to anti-dengue IgG is relatively high for at least a month following infection, but in secondary infection, a rapid increase of IgG antibody generally occurs following infection, and the ratio of anti-dengue IgM to anti-dengue IgG in a single acute specimen is low. U.S. Pat. No. 6,870,032 describes a method for early detection of a flavivirus-induced infection including dengue infection by detecting NS1 protein via enzyme linked immunosorbant assay (ELISA) technique employing at least two antibodies, i.e., a first capture antibody to capture the NS1, and a second antibody for detecting the presence of NS1 in biological samples. However, both HI test and IgG-captured/IgM-captured ELISA usually require paired acute and convalescent phase serum samples collected a week or more apart and a definitive diagnosis is made based on a fourfold rise in anti-dengue antibody. In general, current available dengue diagnostic assays do not allow detection and targeted treatment of DHF during early clinical period. A more rapid test with less reliability on equipment is needed.

Recent advances in global scale proteomics technologies enable the detection of candidate protein biomarkers. These biomarkers include proteins, peptides, or metabolites whose measurement alone (or in a combination) can be used to reliably indicate a disease outcome. With the advancement of multidimensional profiling techniques, the systematic and quick identification of predictive proteins associated with a disease have become feasible.

U.S. Pat. No. 7,939,287 to Tsimikas et al. describe a method of identifying a subject having or at risk of developing coronary artery disease using biomarkers. U.S. Pat. No. 7,608,406 to Valkirs et al. disclose a panel of biomarkers used in a method for early diagnosis and differentiation of stroke types and transient ischemic attacks and for determining prognosis of a patient presenting with stroke symptoms. US Patent No. 7,598,09 to Ray et al. teach methods for diagnosis of Alzheimer's disease by detecting a collection of proteinaceous biomarkers in blood samples.

U.S. Pat. No. 7,629,117 to Avirutnan, et al. disclose methods of determining risk of developing Dengue Hemorrhagic Fever/Dengue Shock Syndrome (DHF/DSS) in an individual infected with dengue virus (DV). The methods comprise determining, in a fluid or tissue sample of an individual, the presence, absence or quantity of dengue virus protein NS1, and determining, in a fluid or tissue sample of the individual, presence, absence or quantity of SC5b-9 complement complex. The methods can further comprise comparing the levels of NS1 protein and SC5b-9 complement complex with a database comprising epidemiological data correlating levels of NS 1 protein and SC5b-9 complement complex with probability of developing DHF/DSS in a population. Complement activation is known to be a key pathogenic mechanism in dengue virus infection. Accelerated complement consumption and marked reduction of plasma complement components are observed in DSS patients during shock. However, the cause of complement activation has remained unknown. Terminal complement complex (SC5b-9) is a group of proteins in the terminal pathway of complement system. It is not always generated when the complement system is triggered due to a tightly-controlled set of the complement regulatory proteins. Only strong or efficient complement activators can successfully cause SC5-9 liberation. In healthy individuals, very low or insignificant level of terminal complement complex can be detected.

Despite the attempts of dengue diagnosis via the detection of selected biomarkers. Identification of predictive biomarkers in complex biofluids, such as plasma, has been challenging for proteomics technologies. Plasma is a complex biofluid, with its constituent proteins present in a broad dynamic concentration range spanning 6 log orders of magnitude or more (25, 26). Moreover, the tendency of high-abundance proteins to adsorb lower-abundance proteins and peptides (27, 28), the presence of proteases that may produce peptide fragments (29, 30), and the individual variation in plasma protein abundances serve to compound the difficulties in comprehensive proteomic analyses of plasma.

SUMMARY OF THE INVENTION

The present invention describes methods for identifying patients with dengue-like symptoms who are at risk of developing dengue hemorrhagic fever. The methods involve measurements of various biomarkers in plasma including IL-10 and seven proteins comprising tropomyosin, complement 4A, immunoglobulin V, fibrinogen, and three isoforms of albumin and determination of likelihood of DHF using MARS modeling strategy. In various configurations, the inventive methods comprise determining, in plasma of an individual presenting dengue-like symptoms the presence, absence or quantity of these biomarkers.

In various configurations, the step of determining presence, absence or quantity of one of these biomarkers comprising (a) contacting a plasma sample from an individual with a solid surface comprising a first probe which specifically binds to one of the targeted biomarker, wherein a complex forms comprising the probe and the that biomarker, if present in the sample, (b) contacting the solid surface with a second probe which specifically binds that biomarker; and (c) determining quantity of the second probe bound to the surface.

In one embodiment, a health care provider such as a medical doctor can make a decision on whether to treat the individual, and which modalities of treatment to use, on the basis of the subject individual's profile of biomarkers including IL-10, tropomyosin, complement 4A, immuno-globulin V, fibrinogen, and three isoforms of albumin in plasma.

In another embodiment, types of probes which can be used in the present methods include, without limitation, antibodies, aptamers, kinases, avimers and combinations thereof. Antibodies can be monoclonal antibodies, polygonal antibodies or combinations thereof, and aptamers can be RNA aptamers, DNA aptamers, peptide aptamers, or combinations thereof.

A solid surface which can comprise a probe can be, without limitation, an ELISA plate, a bead, a dip stick, a test strip or a microarray.

In various aspects, binding of a second probe to a solid surface can be detected using any type of label known to skilled artisans, such as, for example, a fluorophore such as fluorescein, rhodamine, Cy3 or an ALEXA dye of MOLECULAR PROBES™. (Invitrogen, Calif.), a hapten such as biotin or digoxygenin, an enzyme such as horseradish peroxidase, alkaline phosphatase, chloramphenicol acetyltransferase or luciferase, or a radioisotope. In various configurations, a hapten label can be detected by a secondary probe well known to skilled artisans, such as, for example, an enzyme-conjugated antibody directed against biotin or digoxygenin, or an enzyme-conjugated avidin or streptavidin. In addition, binding of a second probe to a solid surface can be quantified using any methods and devices known to skilled artisans, such as, without limitation, measuring fluorescence of a fluorophore linked to a second probe using a fluorimeter, or measuring light absorbance of a chromophore generated by hydrolysis of a chromogenic substrate of an enzyme linked to a secondary probe.

In various embodiments, linkage of a label to a second probe can be direct (for example, an enzyme such as horseradish peroxidase covalently attached to an antibody directed against the target protein or indirect (for example, an enzyme covalently attached to goat anti-mouse serum, when the second probe is a mouse monoclonal antibody directed against the target protein, and when the first probe is not a mouse antibody).

In another embodiment, a kit comprises components to be used to assess an individual's risk of developing DHF. A kit of this embodiment comprises a set of first probes each specifically binds to one of the target biomarker; and a set of second probes which specifically binds that each of the target biomarker. In various aspects of a kit of these embodiments, each probe can be independently selected from the group consisting of an antibody, an aptamer, a kinase, an avimer and a combination thereof. In some aspects, each probe can be an antibody independently selected from the group consisting of a polyclonal antibody and a monoclonal antibody. In some aspects, a second probe comprised by a kit can further comprise a label. However, in some aspects, if a first antibody and a second antibody are directed against the same antigen and the antibodies derive from the same species, the second antibody requires a label which allows it to be detected and quantified independent of detection of the first antibody. Such a label can be, for example, a fluorophore, a hapten such as biotin or digoxygenin, or an enzyme. In addition, a second probe comprised by a kit can comprise a label, which can be, without limitation, a chromophore, a fluorophore, a hapten or an enzyme. An enzyme comprised by a second probe can be, without limitation, horseradish peroxidase, alkaline phosphatase, chloramphenicol acetyltransferase or luciferase. In various embodiments, a kit can further comprise a substrate for the enzyme.

DETAILED DESCRIPTION OF DRAWINGS

FIG. 1A-1B. Differential cytokine expression in dengue fever. Shown is a box-plot comparison of log 2-transformed cytokine values for IL-6 (FIG. 1A), and IL-10 (FIG. 1B) by diagnosis. DF, dengue fever; DHF, dengue hemorrhagic fever. Horizontal bar, median value; shaded box, 25-75% interquartile range (IQR); error bars, median±1.5(IQR);*, outlier.

Figure 2:
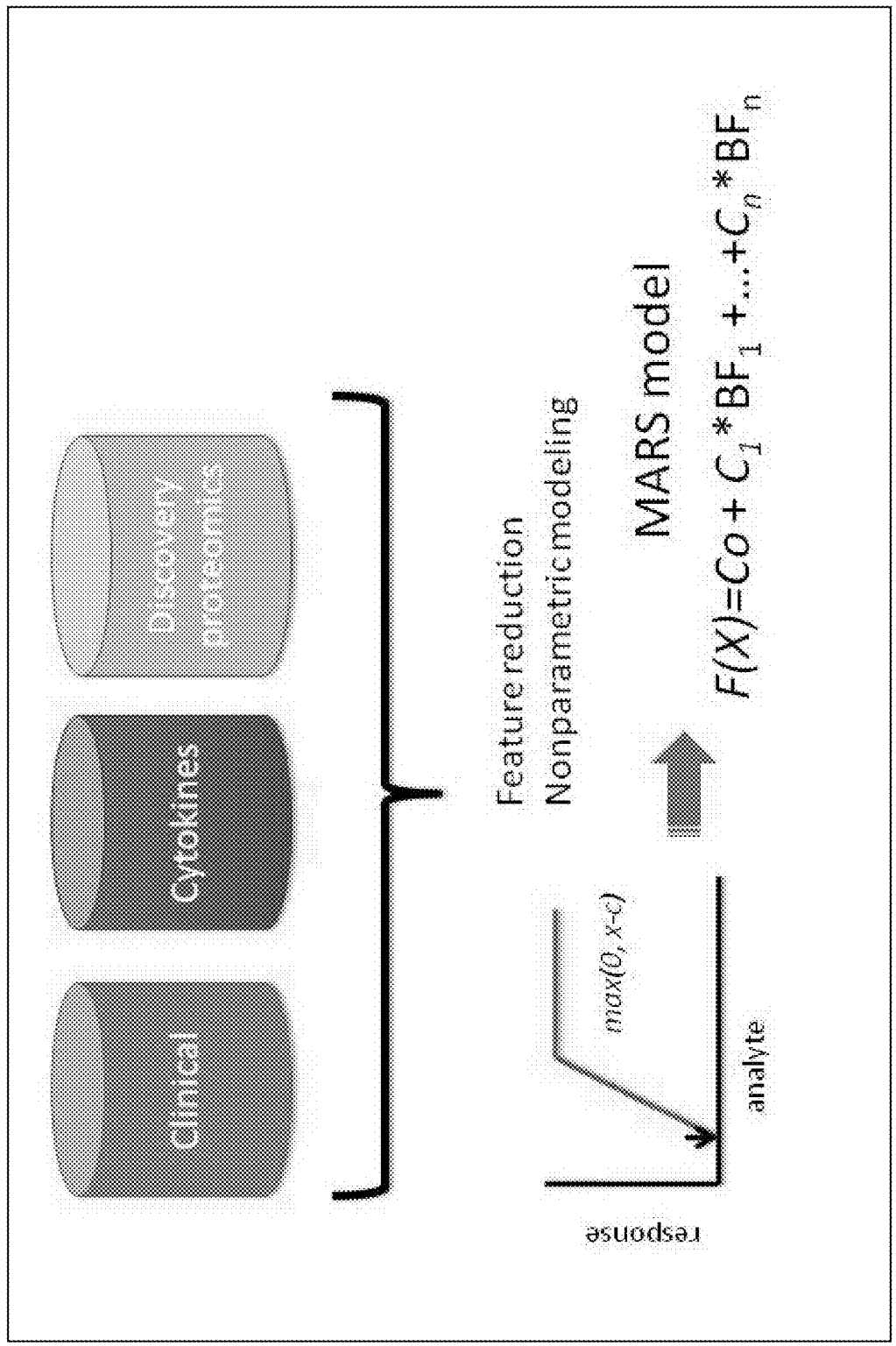

FIG. 2. MARS modeling strategy. Shown is a schematic diagram of modeling strategy to identify predictors of DHF using different data types. Data sources include: clinical demographics, normalized spot intensities by 2DE analysis and log 2-transformed cytokine measurements. MARS produces a linear combination of basis functions (BFs), each represented by the value of the maximum of (0, x-c), where x is the analyte concentration.

Figure 3:
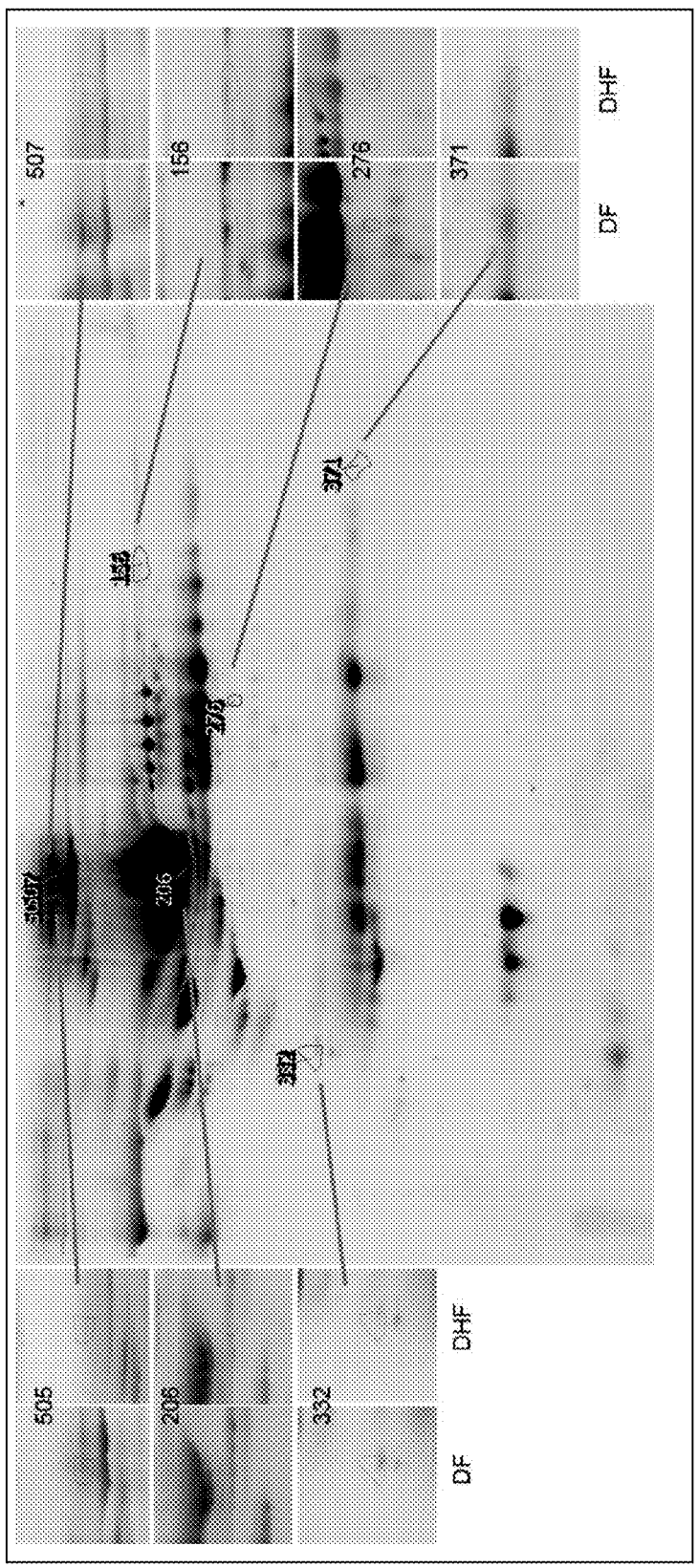

FIG. 3. 2DE images. Shown is a reference gel of 2DE of BAP fractionated and IgY depleted plasma from the study subjects. The locations of protein spots that contribute to the prediction of DHF are indicated. Insets, spot appearances for reference gels for DHF and DF. Spot 156 (C4A), 206 (albumin*1), 276 (fibrinogen), 332 (tropomyosin), 371 (immunoglobulin gamma-variable region), 506 (albumin*2) and 507(albumin*3).

Figure 4:
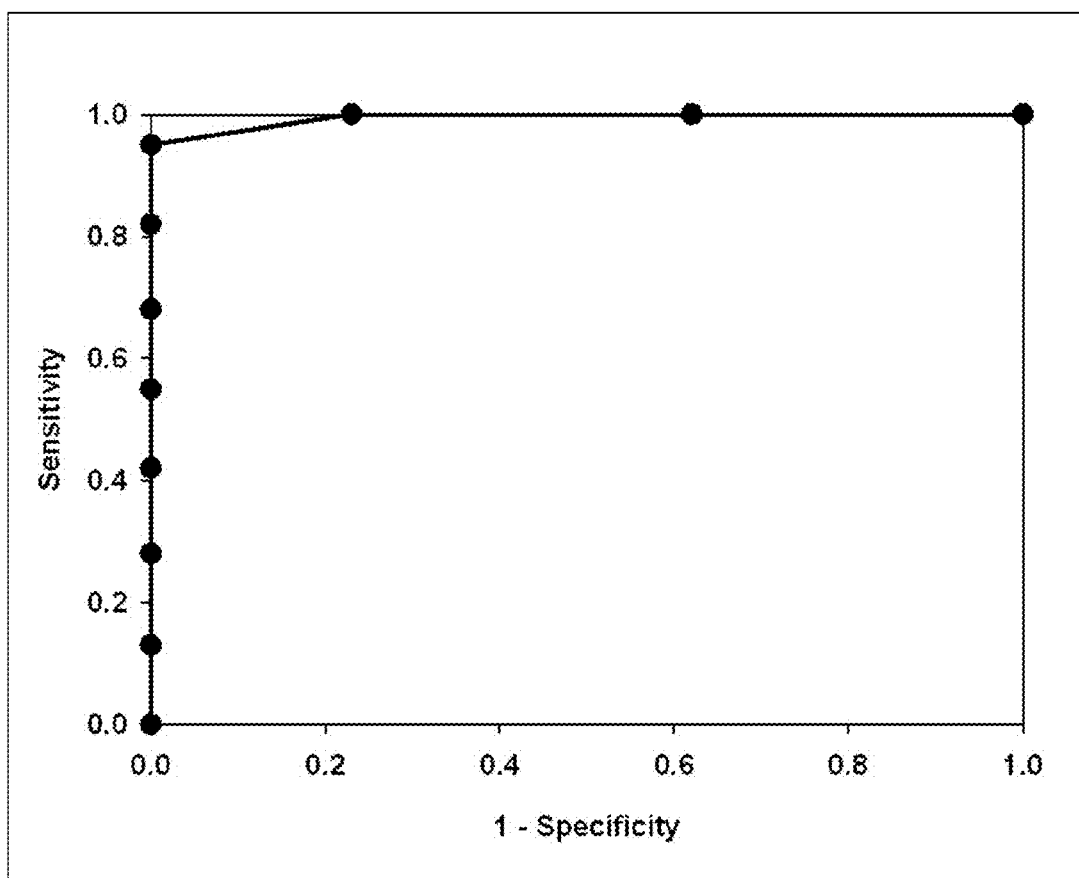

FIG. 4. ROC analysis. Shown is a Receiver Operating Characteristic (ROC) curve for the predictive model for DHF. Y axis, Sensitivity; X axis, 1-Specificity.

Figure 5:
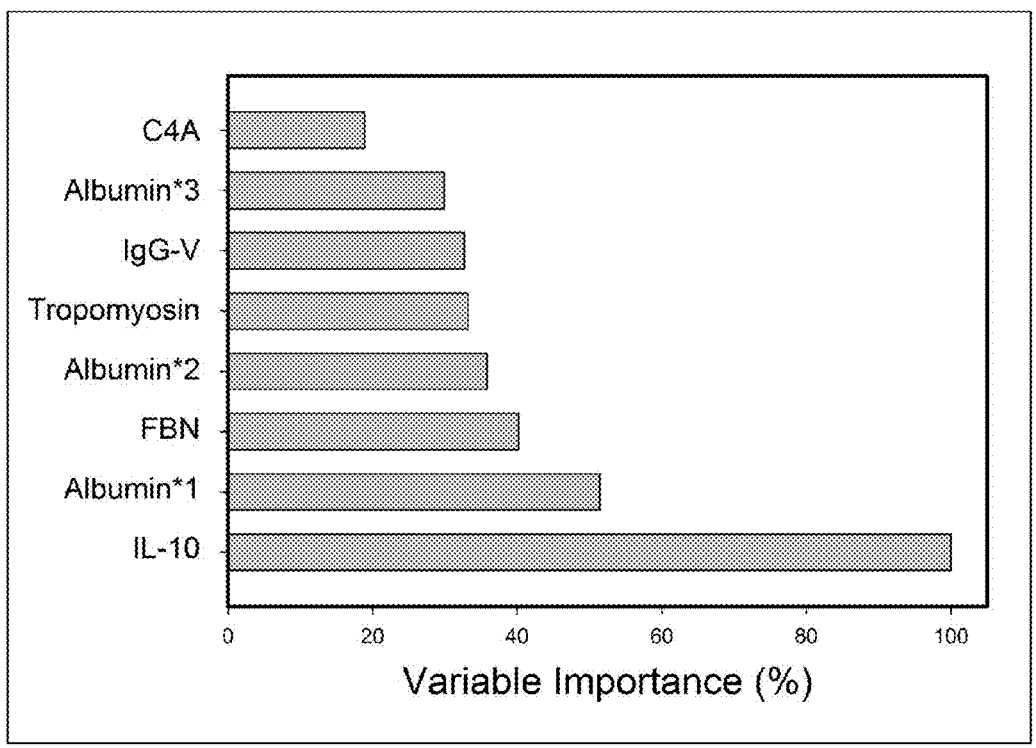
Figure 6A:
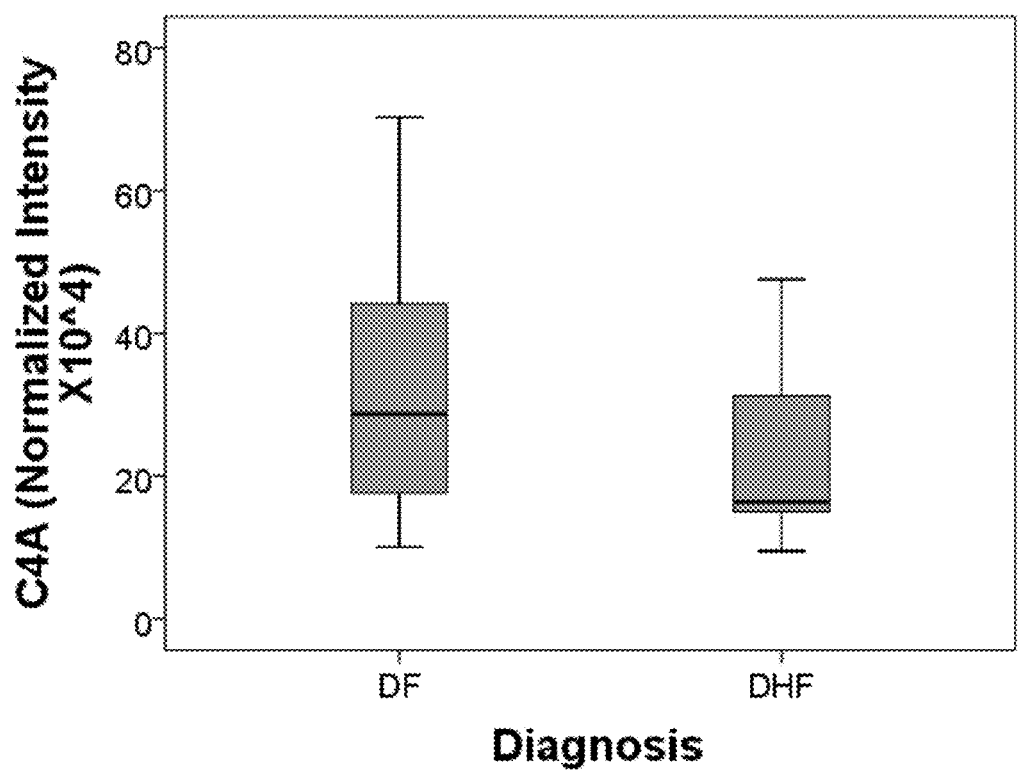
Figure 6D:
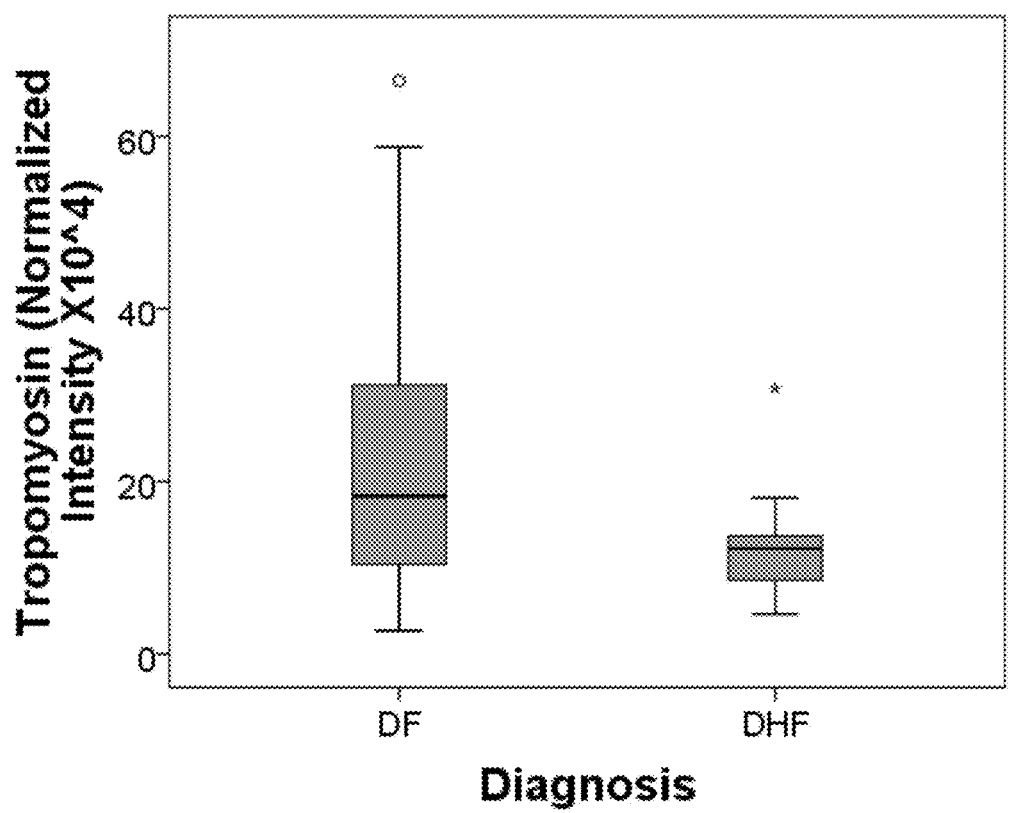
Figure 6E:
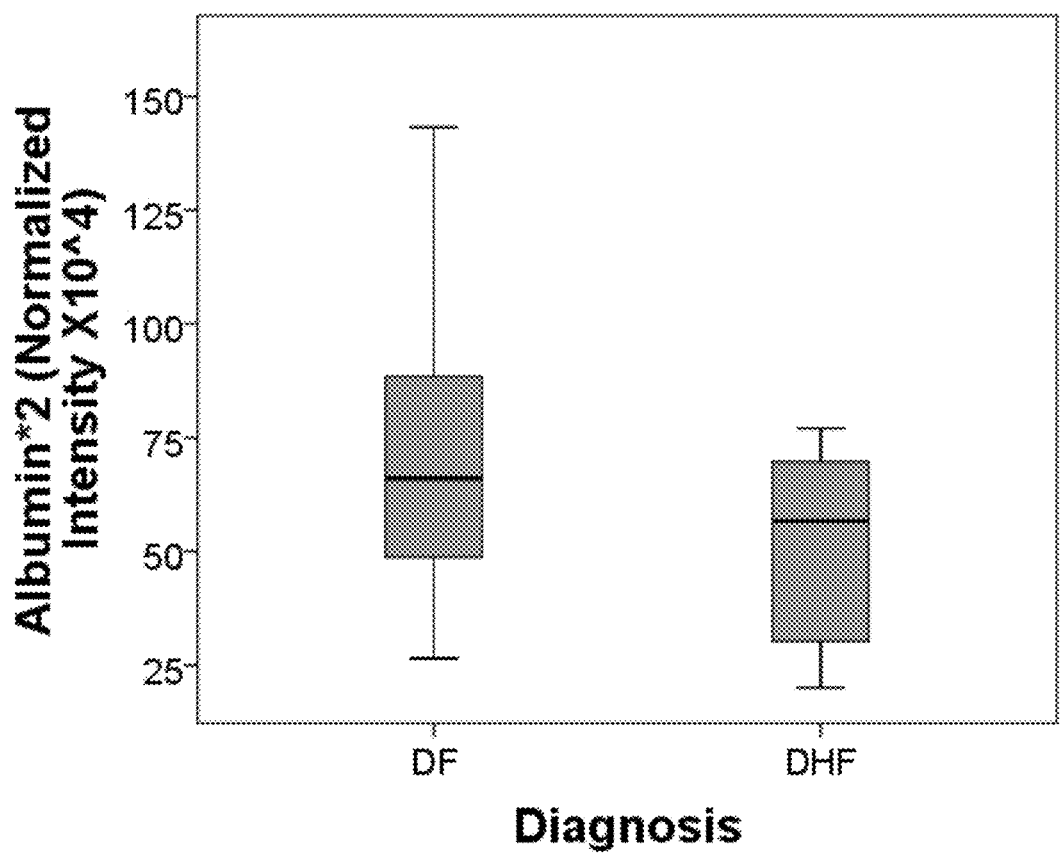
Figure 6F:
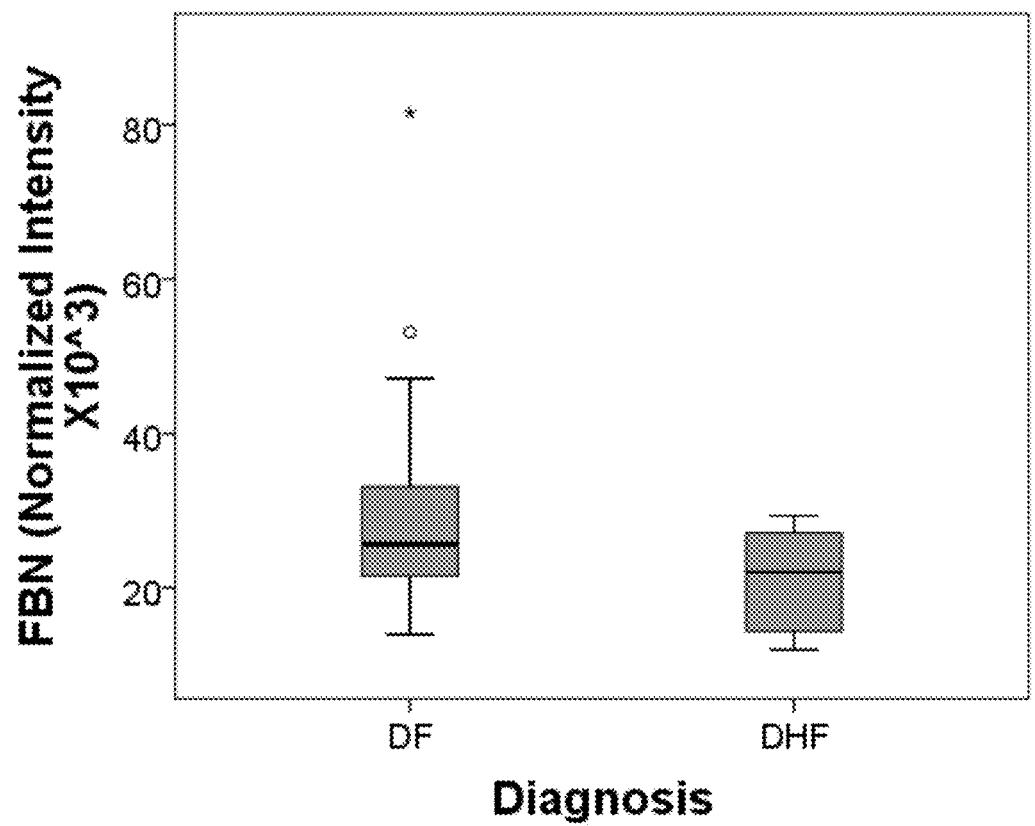
Figure 7A:
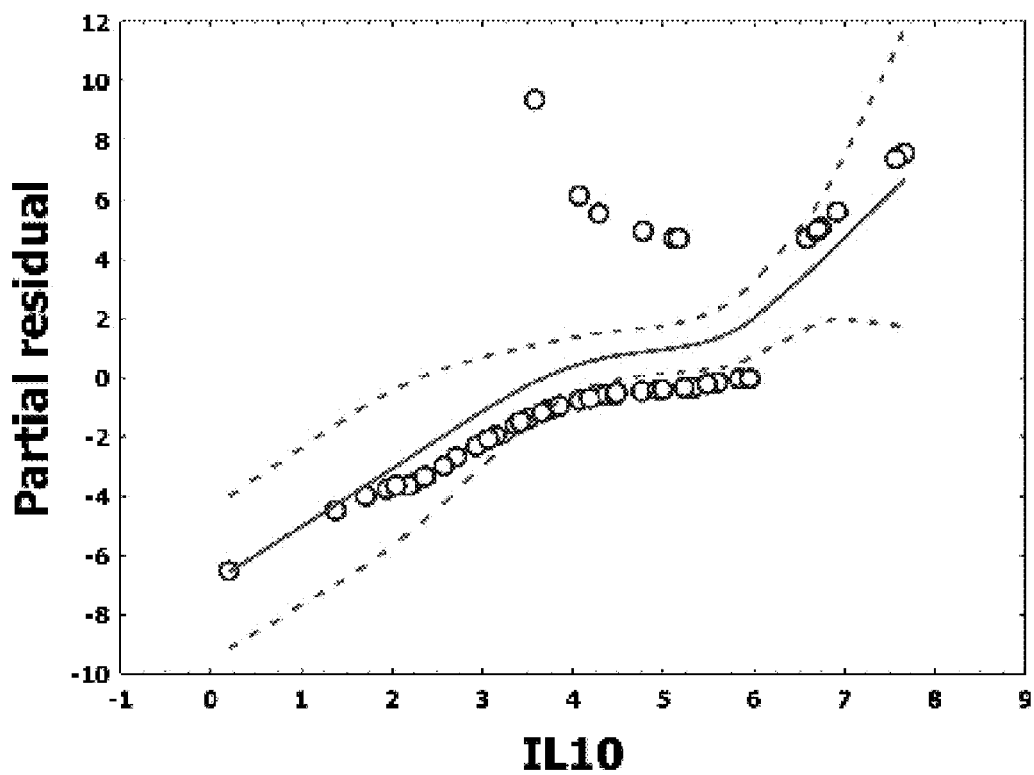
Figure 7B:
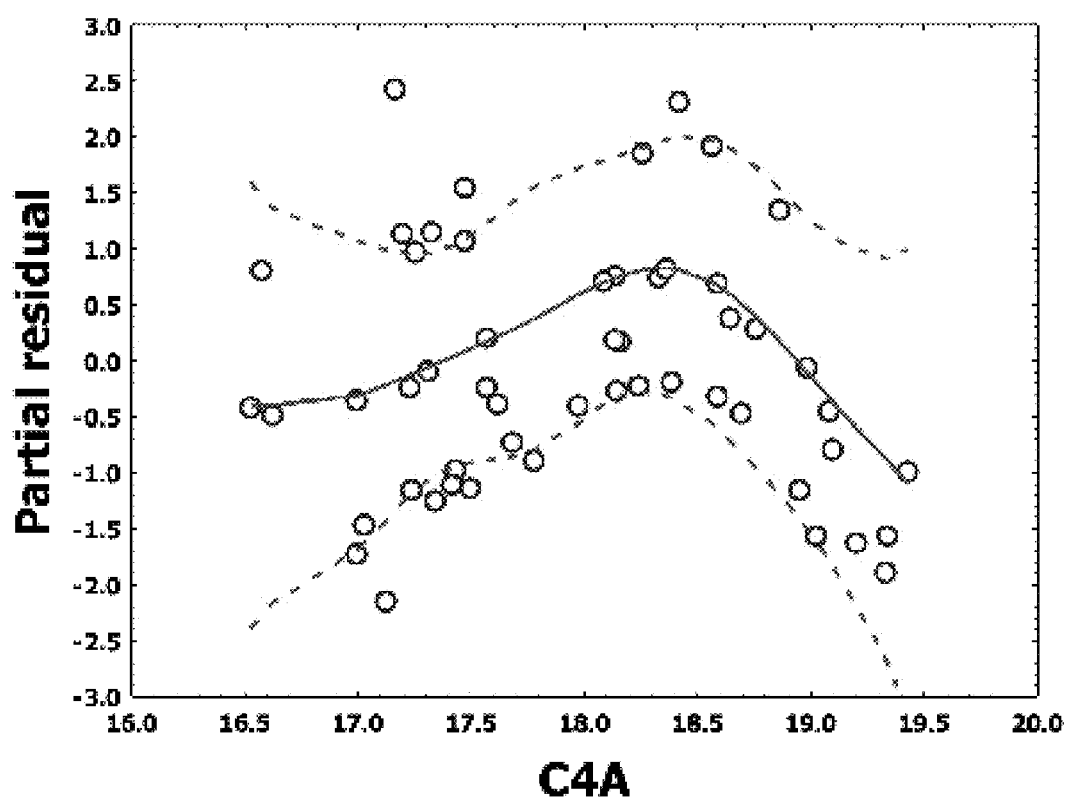
Figure 7C:
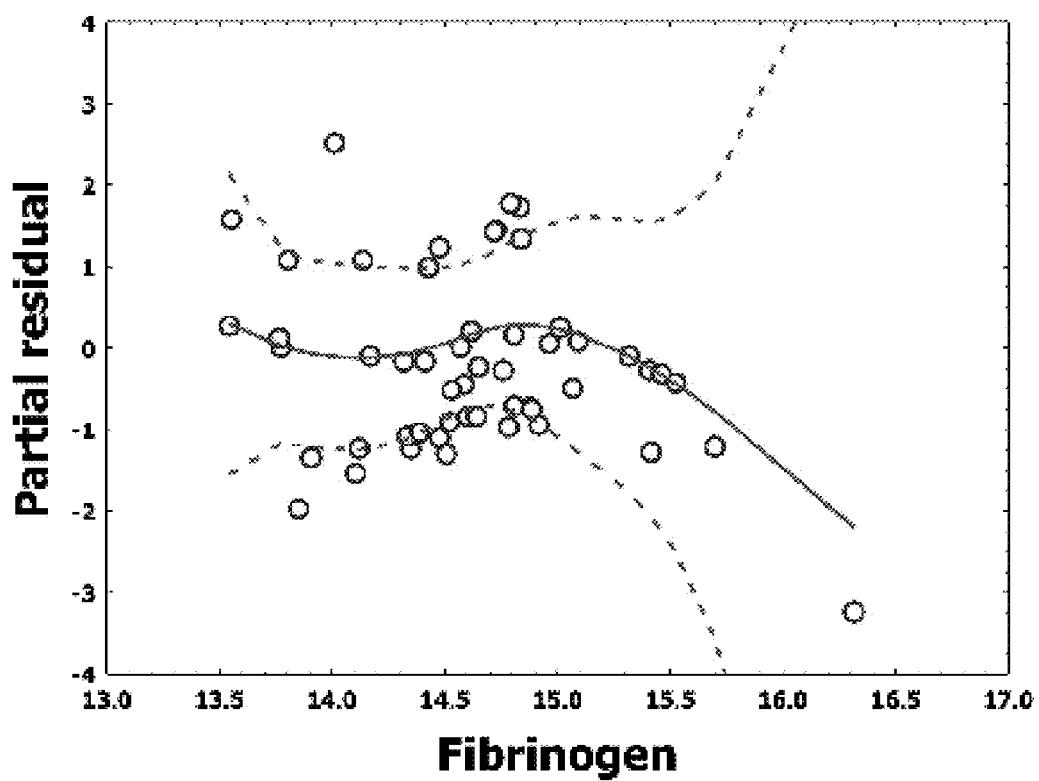
Figure 7D:
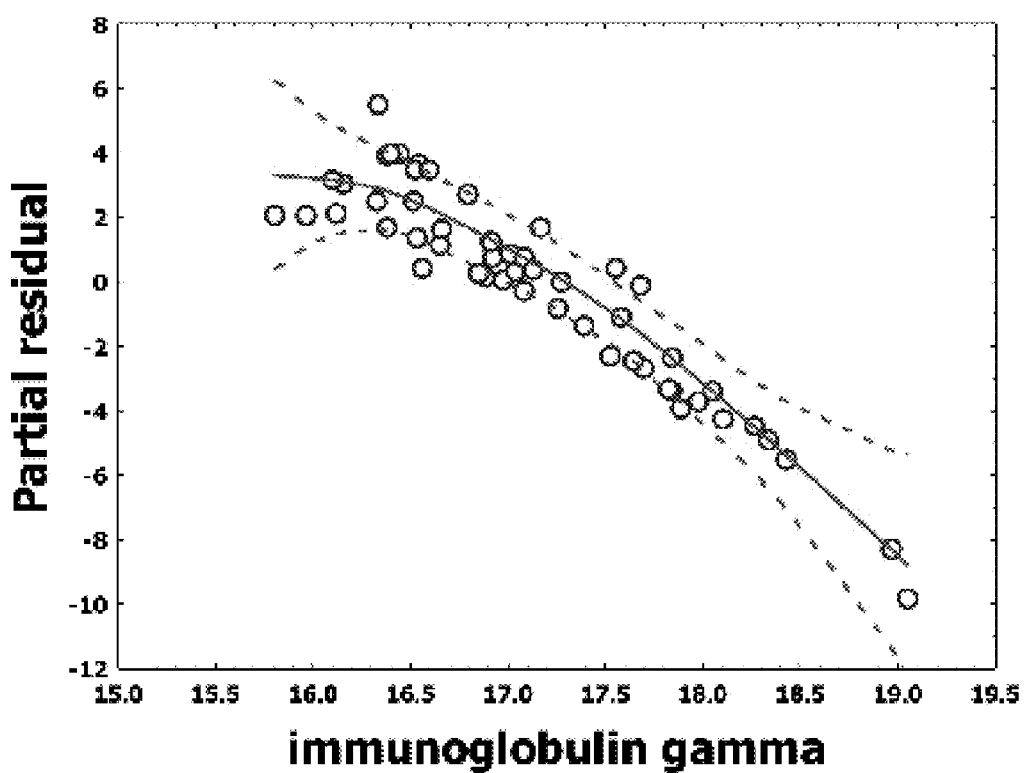
Figure 7E:
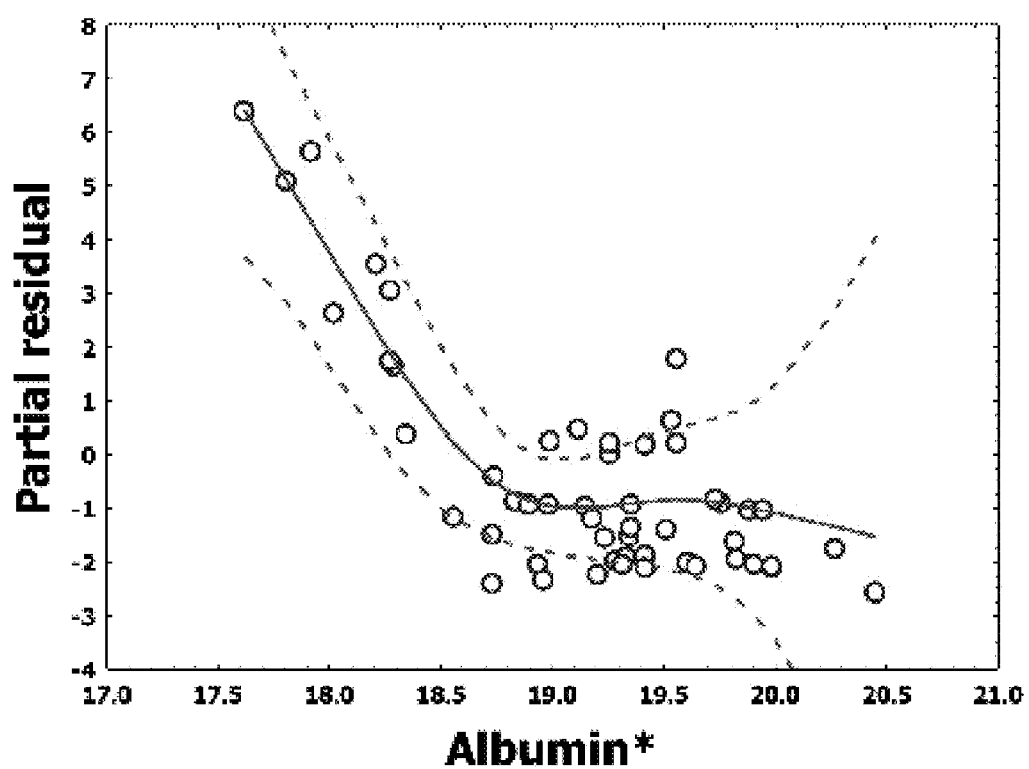
Figure 7F:
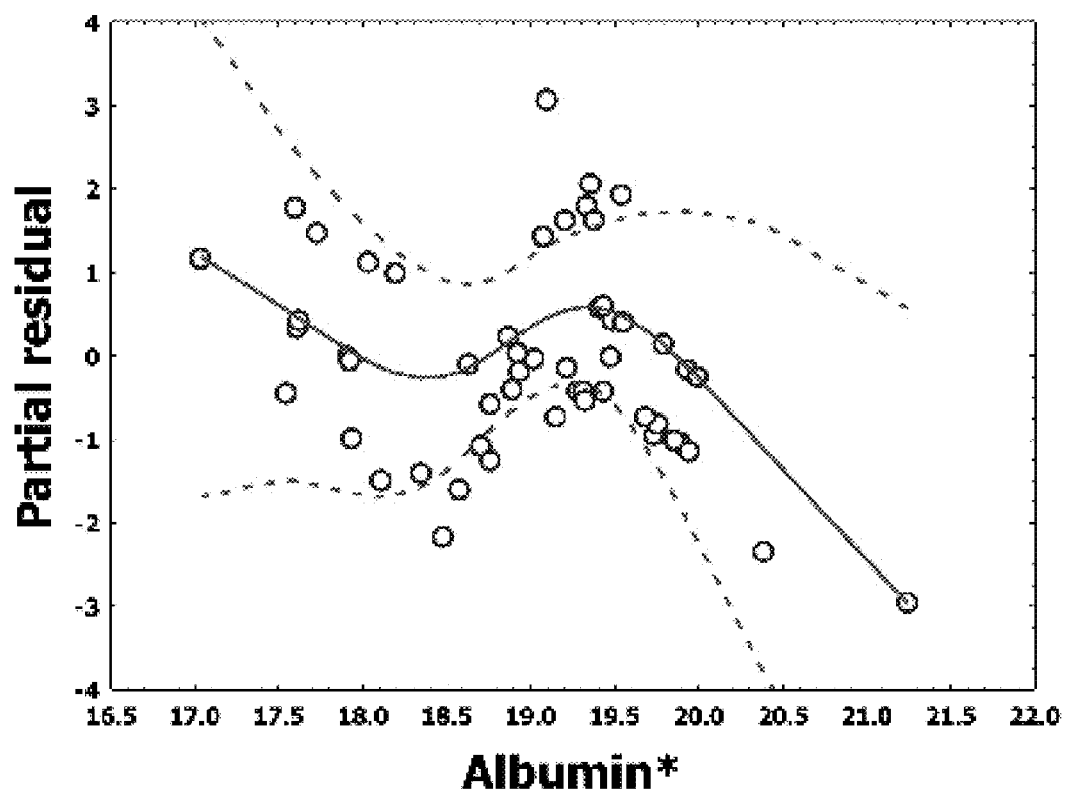

FIG. 5. Variable Importance for MARS model of DHF. Variable importance was computed for each feature in the MARS model. Y axis, percent contribution for each analyte.

FIG. 6A-6G. Differential 2DE spot expression in dengue fever. Shown is a box-plot comparison of 2DE spot expression values for C4A (FIG. 6A), Albumin*3 (FIG. 6B), IgG-V (FIG. 6C), Tropomyosin (FIG. 6D), Albumin*2 (FIG. 6E), fibrinogen (FBN, FIG. 6F), and Albumin*1 (FIG. 6G) by diagnosis. DF, Dengue fever; DHF, Dengue hemorrhagic fever. Horizontal bar, median value; shaded box, 25-75% interquartile range (IQR); error bars, median±1.5(IQR);*, outlier.

FIG. 7A-7F. Generalized Additive Model analysis. Shown are the partial residual plots for log-transformed values of 8 proteins important in MARS classifier. Y axis, partial residuals; X axis, log of respective feature. Note that regional deviations from classical linear model assumptions are seen.

Figure 8:
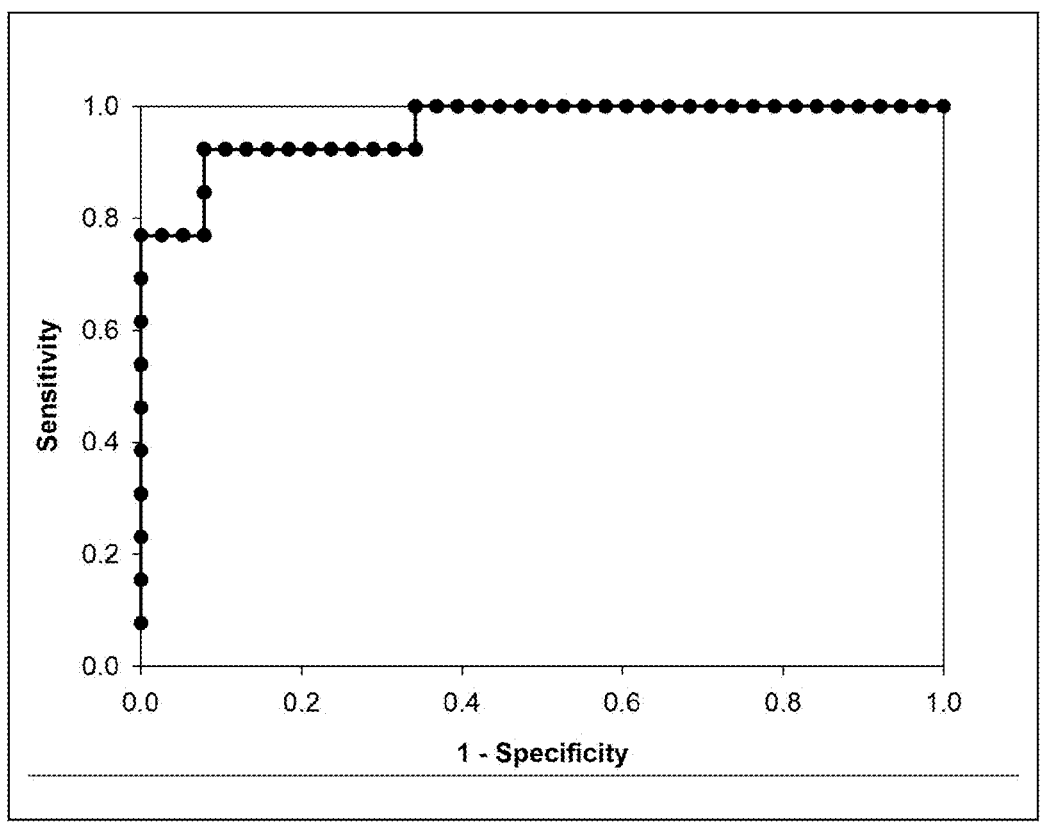

FIG. 8. Receiver Operating Characteristic (ROC) Curve for the LR model of DHF. Shown is an ROC curve for the LR predictive model for DHF. Y axis, Sensitivity; X axis, 1-Specificity.

Figure 9A:
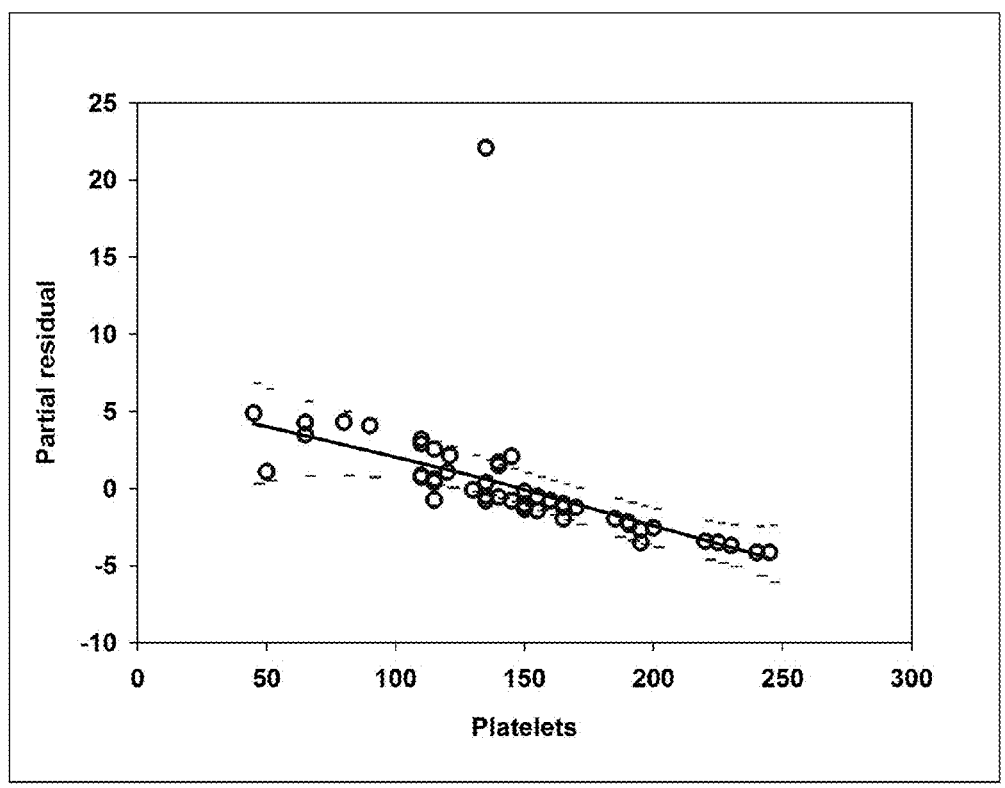
Figure 9B:
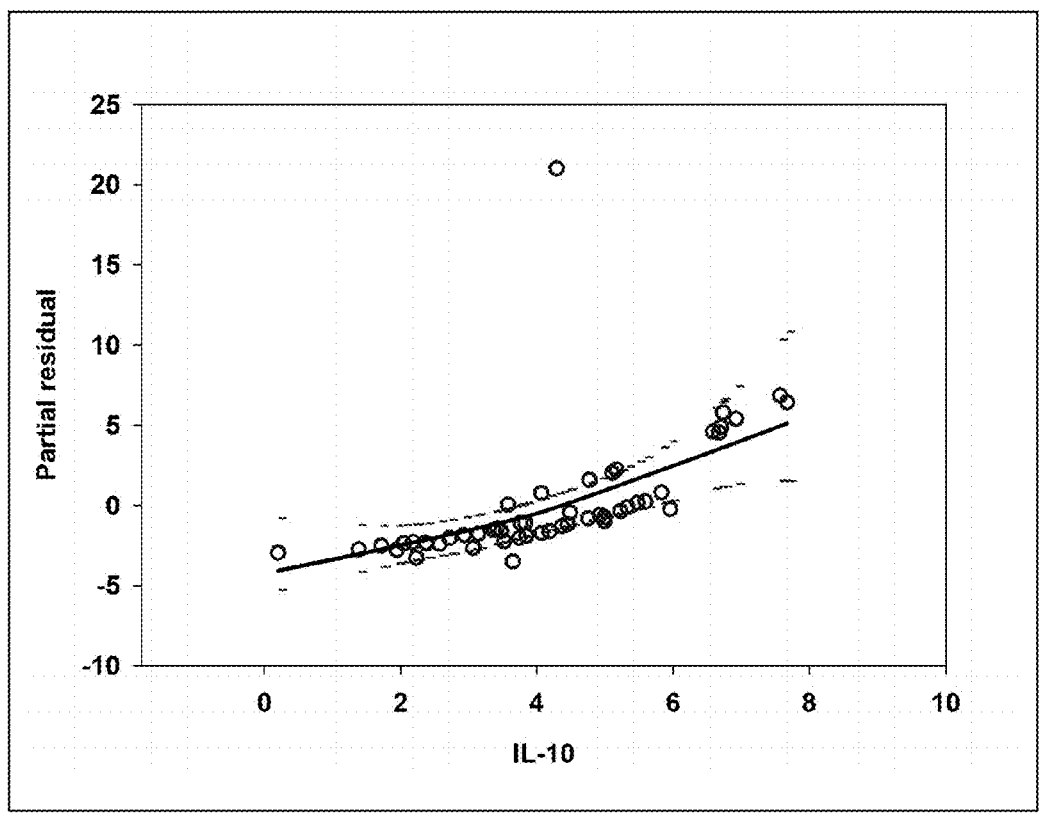
Figure 9C:
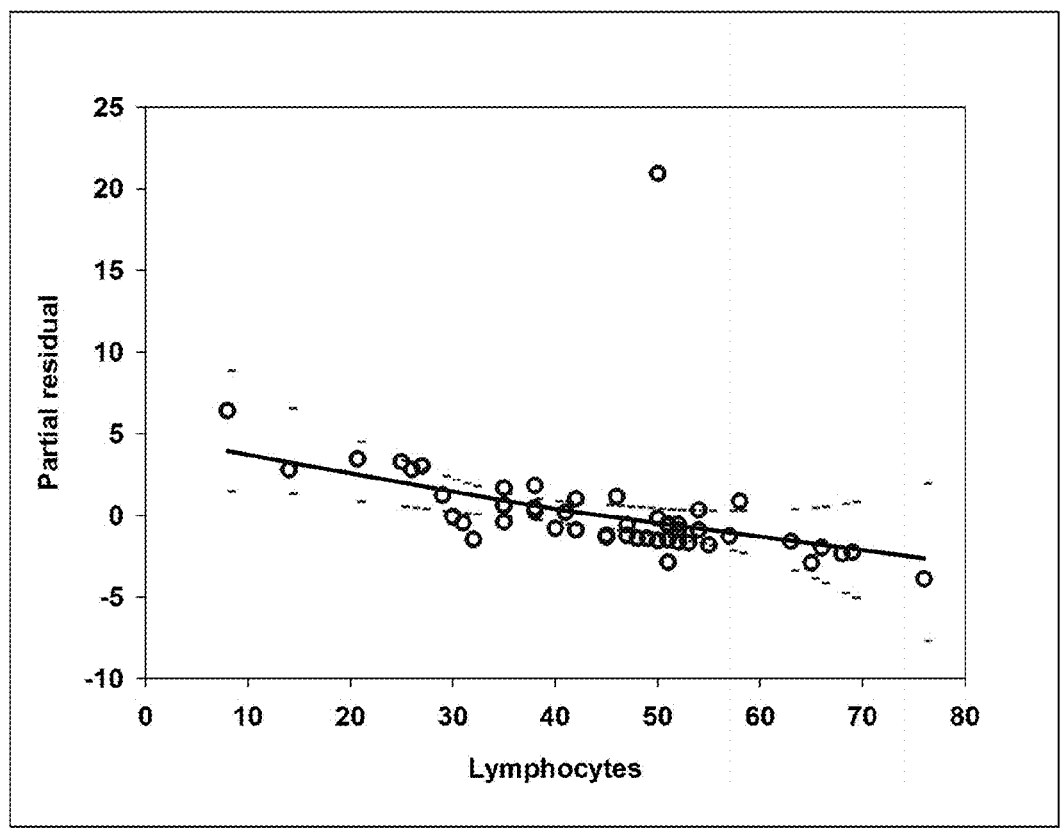

FIG. 9A-9C. Model Diagnostics for GAM fits. Shown are partial residual plots for each feature in the logistic regression model. Each subject is indicated by a circle. The observations that could potentially influence the model are the 23rd and 51th observations. Dashed lines are 95% confidence intervals. A=platelets, B=LIL10, C=Lymphocytes.

Figure 10:
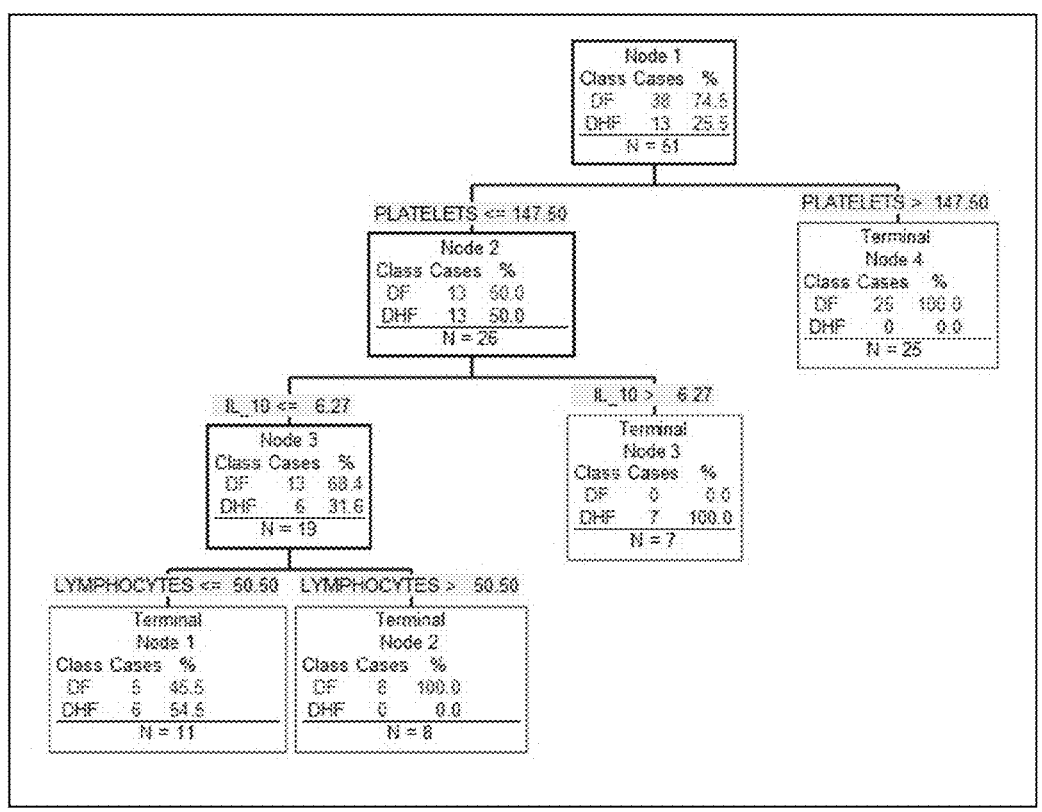

FIG. 10. Classification and regression tree (CART) for prediction of DHF. Shown is a CART decision tree for classification of DHF.

DETAILED DESCRIPTION OF THE INVENTION

A biomarker is an organic biomolecule that present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

In this invention, parameters including clinical signs, laboratory measures, plasma proteins and cytokine concentration at the time of the initial dengue presentation were compared between dengue fever and DHF outcomes. Models for predicting presenting patients who are at risk for developing DHF is build and validated. Biomarkers that are most informative of DHF and to be used with the models were identified.

An embodiment of a method for identifying patients at risk of developing DHF, comprising:
1) obtaining a plasma sample from a patient with presenting symptoms of dengue infection;
2) detecting the concentration of IL-10, tropomyosin, complement 4A, immunoglobulin V, fibrinogen, albumin*1, albumin*2 and albumin*3 in said sample; and
3) correlating a patient's risk of developing DHF to concentrations of IL-10, tropomyosin, complement 4A, immunoglobulin V, fibrinogen, albumin*1, albumin*2 and albumin*3 in said sample based on MARS DHF model.

In various configurations, the methods comprise determining, in plasma of an individual presenting symptoms of dengue disease the presence, absence or quantity of biomarkers including IL-10 and seven proteins including tropomyosin, complement 4A, immunoglobulin V, fibrinogen, and three isoforms of albumin. In various aspects, an individual is considered to be at risk of developing DHS if these biomarkers are fit the MARS DHF model.

In various configurations, determining presence, absence or quantity of one of these seven proteins can comprise (a) contacting a plasma sample from an individual with a solid surface comprising a first probe which specifically binds to one of the targeted biomarker, wherein a complex forms comprising the probe and the that biomarker, if present in the sample, (b) contacting the solid surface with a second probe which specifically binds that biomarker; and (c) determining quantity of the second probe bound to the surface.

In one embodiment, a health care provider such as a medical doctor can make a decision on whether to treat the individual, and which modalities of treatment to use, on the basis of the subject individual's profile of biomarkers including IL-10, tropomyosin, complement 4A, immunoglobulin V, fibrinogen, and three isoforms of albumin in plasma.

In another embodiment, types of probes which can be used in the present methods include, without limitation, antibodies, aptamers, kinases, avimers and combinations thereof. Antibodies can be monoclonal antibodies, polygonal antibodies or combinations thereof, and aptamers can be RNA aptamers, DNA aptamers, peptide aptamers, or combinations thereof.

A solid surface which can comprise a probe can be, without limitation, an ELISA plate, a bead, a dip stick, a test strip or a microarray.

In various aspects, binding of a second probe to a solid surface can be detected using any type of label known to skilled artisans, such as, for example, a fluorophore such as fluorescein, rhodamine, Cy3 or an ALEXA dye of MOLECULAR PROBES™ (Invitrogen, Calif.), a hapten such as biotin or digoxygenin, an enzyme such as horseradish peroxidase, alkaline phosphatase, chloramphenicol acetyltransferase or luciferase, or a radioisotope. In various configurations, a hapten label can be detected by a secondary probe well known to skilled artisans, such as, for example, an enzyme-conjugated antibody directed against biotin or digoxygenin, or an enzyme-conjugated avidin or streptavidin. In addition, binding of a second probe to a solid surface can be quantified using any methods and devices known to skilled artisans, such as, without limitation, measuring fluorescence of a fluorophore linked to a second probe using a fluorimeter, or measuring light absorbance of a chromophore generated by hydrolysis of a chromogenic substrate of an enzyme linked to a secondary probe.

In various embodiments, linkage of a label to a second probe can be direct (for example, an enzyme such as horseradish peroxidase covalently attached to an antibody directed against the target protein or indirect (for example, an enzyme covalently attached to goat anti-mouse serum, when the second probe is a mouse monoclonal antibody directed against the target protein, and when the first probe is not a mouse antibody).

In another embodiment, a kit comprises components to be used to assess individual risk of developing DHF. A kit of this embodiment comprises a set of first probes each specifically binds to one of the target biomarker; and a set of second probes which specifically binds that each of the target biomarker. In various aspects of a kit of these embodiments, each probe can be independently selected from the group consisting of an antibody, an aptamer, a kinase, an avimer and a combination thereof. In some aspects, each probe can be an antibody independently selected from the group consisting of a polyclonal antibody and a monoclonal antibody. In some aspects, a second probe comprised by a kit can further comprise a label. However, in some aspects, if a first antibody and a second antibody are directed against the same antigen and the antibodies derive from the same species, the second antibody requires a label which allows it to be detected and quantified independent of detection of the first antibody. Such a label can be, for example, a fluorophore, a hapten such as biotin or digoxygenin, or an enzyme. In addition, a second probe comprised by a kit can comprise a label, which can be, without limitation, a chromophore, a fluorophore, a hapten or an enzyme. An enzyme comprised by a second probe can be, without limitation, horseradish peroxidase, alkaline phosphatase, chloramphenicol acetyltransferase or luciferase. In various embodiments, a kit can further comprise a substrate for the enzyme.

Example 1: Identification of Biomarkers of DHF and Nonparametric DHF Modeling

To identify differentially expressed proteins associated with DHF, a reproducible, novel pre-separation fractionation method is developed, and is termed the biofluid analysis platform (BAP). BAP takes advantage of high recovery and quantitative size exclusion fractionation, followed by quantitative saturation fluorescence labeling, two dimensional gel electrophoresis (2-DE), and LC-MS/MS (liquid chromatography-tandem mass spectrometry) protein identification to identify differentially expressed proteins associated with DHF.

Plasma samples from 53 volunteers (42 DF and 13 DHF) with initial clinical presentation of dengue infection were obtained and subjected to focused and discovery-based proteomic using ELISA and BAP.

Demographics, clinical laboratory measurements, 9 cytokines and 419 plasma proteins at the time of initial presentation were compared between the outcomes of dengue fever and dengue hemorrhagic fever. Statistical comparison showed that the subject's gender, clinical parameters, 2 cytokines and 42 proteins discriminated between the groups, but importantly, gender contributed significant interactions. Because statistical analysis of discriminate proteins indicates that the proteins are not normally distributed, conventional parametric modeling approaches is precluded. These factors were reduced by a nonparametric classification approach, multivariate adaptive regression splines (MARS), where a highly accurate classifier of the sample set including IL-10 and 7 plasma proteins was obtained as biomarkers for DHF using cross-validation.

Sample Collection and Preparation

An active surveillance for dengue diseases study was conducted in Iquitos, Peru, and Maracay, Venezuela. Febrile subjects with signs and symptoms consistent with dengue virus infection were included in the study (Forshey et al. 2010). On the day of presentation, a blood sample was collected for dengue virus RT-PCR confirmation, and plasma preparation. Viral RNA was prepared from 140 µl sera using QIAamp Viral RNA Mini Kits following the manufacturer's instructions (QIAGEN® Inc., Valencia, Calif.). Nested dengue virus RT-PCR was performed following the protocol of Lanciotti et al. (1992) on serum samples for dengue virus detection. The subjects were monitored for clinical outcome. DF and DHF cases were scored following WHO case definitions. An additional blood sample was collected on study day 30 for plasma preparation. Plasma specimens were stored at −70° C. until proteomic processing. Numbers of patients and disease characteristics are shown in Table I. The initial clinical parameters were compared for the 55 volunteers (42 DF, 13 DHF) at the time of initial presentation (Table I). Here, the number of days of fever (4.2±1 d vs 5±1 d, p<0.01), initial platelet counts (161±40.7×10$^3$/ml vs 105±33×10$^3$/ml), red blood count (4.56±13.68 vs 3±1.37) and frequency of diarrhea (46% vs 14%) were statistically different between DF and DHF, respectively (p=x).

TABLE I

| Clinical characteristics of study population. | | | | |
|---|---|---|---|---|
| Phenotype | Characteristic | No. of men = 23 (42%) | No. of women = 32 (58%) | All subjects = 55 |
| DHF (n = 13) | | n = 3 (23%) | n = 10 (77%) | n = 13 |
| | Age (years) | 24 ± 22 | 18 ± 11 | 19 ± 13.4 |
| | Weight (kg) | 46 ± 6.6 | 42 ± 9.3 | 45 ± 14 |
| | Temp max (° C.) | 39.1 ± 1.04 | 39 ± 0.65 | 39 ± 0.70 |
| | Fever (days) | 6 ± 1.73 | 5 ± 0.66 | 5 ± 1b |
| | Hemoglobin (gm %) | 12.83 ± 0.83 | 12 ± 0.97 | 12 ± 0.93a |
| | Hematocrit (%) | 41.16 ± 1.89 | 39 ± 3.68 | 39 ± 3.5 |
| | Platelets (103/µL) | 125.33 ± 13 | 99 ± 35 | 105 ± 33c |

TABLE I-continued

Clinical characteristics of study population.

| Phenotype | Characteristic | No. of men = 23 (42%) | No. of women = 32 (58%) | All subjects = 55 |
|---|---|---|---|---|
| | RBC (×106/μL) | 2.6 ± 0.6 | 4 ± 1.48 | 3 ± 1.37a |
| | Lymphocytes (103/μL) | 29.5 ± 11 | 39 ± 15.6 | 37 ± 14.8 |
| | Neutrophils (103/μL) | 66.1 ± 7.25 | 59 ± 14.98 | 61 ± 13.65 |
| | Diarrhea | 67% | 40% | 46%a |
| DF (n = 42) | | n = 20 (47%) | n = 22 (52%) | n = 42 |
| | Age (years) | 14.35 ± 7.05 | 16.7 ± 7.9 | 15.59 ± 7.5 |
| | Weight (kg) | 42.5 ± 17.67 | 33.4 ± 12.4 | 36 ± 13 |
| | Temp max (° C.) | 39.07 ± 0.66 | 38.72 ± 0.65 | 38.8 ± 0.67 |
| | Fever (days) | 4.5 ± 1.05 | 4.08 ± 1.11 | 4.2 ± 1 |
| | Hemoglobin (gm %) | 13.96 ± 1.73 | 13.22 ± 1.32 | 13.57 ± 1.56 |
| | Hematocrit (%) | 42.7 ± 4.53 | 40.27 ± 4.24 | 41.42 ± 4.5 |
| | Platelets (103/μL) | 167.25 ± 35.7 | 155.4 ± 45 | 161 ± 40.7 |
| | RBC (×106/μL) | 4.70 ± 1.88 | 4.46 ± 2.1 | 4.56 ± 1.98 |
| | Lymphocytes (103/μL) | 42.45 ± 12.25 | 48.45 ± 14.5 | 45.6 ± 13.68 |
| | Neutrophils (103/μL) | 56.1 ± 12.62 | 50.54 ± 14.44 | 53.19 ± 13.73 |
| | Diarrhea | 10% | 18% | 14% |

DHF = dengue hemorrhagic fever;
DF = dengue fever;
n = number;
RBC = red blood cell count.
a$p < 0.05$;
b$p < 0.01$;
c$p < 0.001$.

Multiplex Bead-Based Cytokine Measurements

Plasma samples were analyzed for the concentrations of 9 human cytokines (IL-6, IL-10, IFN-β, IP-10, MIP-1α, TNFα, IL-2, VEGF, and TRAIL (Bioplex, Bio-Rad, Hercules, Calif.). Plasma samples were thawed, centrifuged at 4,500 rpm for 3 minutes at 4° C., and incubated with microbeads labeled with antibodies specific to each analyte for 30 minutes. Following a wash step, the beads were incubated with the detection antibody cocktail, each bead specific to a single cytokine. After another wash step, the beads were incubated with streptavidin-phycoerythrin for 10 minutes and washed again. The analyte concentrations were determined using the array reader. For each analyte, a standard curve was generated using recombinant proteins to estimate protein concentration in the unknown sample.

Biofluid Analysis Platform Pre-Separation Fractionation

The Biofluids Analytical Platform (BAP) pre-separation fractionation system is a semiautomated and custom-designed device consisting of four 1×30 cm columns fitted with upward flow adapters and filled with Superdex S-75 (GE Healthcare, Pittsburgh, Pa.) size-exclusion beads. Samples were injected into each column through four HPLC injectors, and buffer flow was controlled by an HPLC pump (Model 305, GILSON®, Middleton, Wis.). The effluent from each column was monitored by individual UV/Vis monitors (Model 251, GILSON®, Middleton, Wis.) that each control individual fraction collectors (Model 203B, GILSON®, Middleton, Wis.). The columns were equilibrated with Running Buffer (50 mM $(NH_4)_2CO_3$, pH 8.0), and up to three hundred microliters of plasma, containing 3 mg of protein and 8M urea spiked with 3 μg of purified Alexa-488 labeled thaumatin (Sigma-Aldrich, St. Louis, Mo.), are pumped into the columns at an upward flow rate of 20 ml/hour. The effluent was monitored at 493 nm by the UV/V is monitor that was programmed to detect a predetermined signal of 0.1 mV in the detector output that designated the start and end of the fluorescent thaumatin peak, and signaled the fraction collector to change collection tubes after an appropriate delay. The fractions preceding the end of the thaumatin peak were pooled and designated the "protein pool," while the fractions subsequent to the peak up to the free dye peak were pooled and designated the "peptide pool."

After size-exclusion chromatography (SEC), the protein pools were incubated at 4° C. overnight to permit further renaturation. They were then loaded onto antibody (IgY) depletion columns per the manufacturer's instructions (PHENOMENEX®, Torrance, Calif.) to deplete fourteen of the most highly abundant proteins found in plasma or serum. The flow-through was collected and re-run through the columns a second time. The proteins obtained from the second flow-through were concentrated and resuspended in 2-DE buffer for quantitative saturation fluorescence labeling.

Saturation Fluorescence Labeling

A saturation fluorescence approach was developed using uncharged BODIPY FL-maleimide (BD) that reacts with protein thiols at a dye-to-protein thiol ratio of greater than 50:1 to give an uncharged product, with no non-specific labeling. BD-labeled protein isoelectric points are unchanged and mobilities were identical to those in the unlabeled state. Using the ProExpress 2D imager (PERKINELMER®, Cambridge, UK), BD protein labeling (ex: 460/80 nm; em: 535/50 nm) has a dynamic range over 4 log orders of magnitude, and can detect 5 fmol of protein at a signal-to-noise ratio of 2:1. This saturation fluorescence labeling method has yielded high accuracy (>91%) in quantifying blinded protein samples (11). To ensure saturation labeling, protein extracts or pools to be labeled were analyzed for cysteine (cysteic acid) content by amino acid analysis (Model L8800, Hitachi High Technologies America, Pleasanton, Calif.) and sufficient dye added to achieve the desired excess of dye to thiol.

BD-labeled proteins were separated by 2DE (O'Farrell, 1975), employing an IPGphor multiple sample IEF device (PHARMACIA, Piscataway, N.J.) in the first dimension, and Protean Plus and Criterion Dodeca cells (Bio-Rad, Hercules, Calif.) in the second dimension. Sample aliquots were first loaded onto 11 cm dehydrated precast immobilized pH gradient (IPG) strips (Bio-Rad), and rehydrated overnight. IEF was performed at 20° C. with the following parameters: 50 Volts, 11 hours; 250 Volts, 1 hour; 500 Volts, 1 hour; 1000 Volts, 1 hour; 8000 Volts, 2 hours; 8000 Volts, 6 hour. The IPG strips were then be incubated in 4 mL of equilibration buffer (6 M urea, 2% SDS, 50 mM Tris-HCl, pH 8.8, 20% glycerol) containing 10 µl/mL tri-2 (2-carboxyethyl) phosphine (Geno Technology, Inc., St. Louis, Mo.) for 15 minutes at 22° C. with shaking. The samples were incubated in another 4 mL of equilibration Buffer with 25 mg/mL iodoacetamide for 15 min at 22° C. with shaking in order to ensure protein S-alkylation. Electrophoresis is performed at 150V for 2.25 h, 4° C. with precast 8-16% polyacrylamide gels in Tris-glycine buffer (25 mM Tris-HCl, 192 mM glycine, 0.1% SDS, pH 8.3).

Protein Fluorescence Staining

After electrophoresis, the gels were directly imaged at 100 µm resolution using the PERKINELMER® ProXPRESS 2D Proteomic Imaging System to quantify BD-labeled proteins (>90% of human proteins contain at least one cysteine (12)). A gel containing the most common features was selected by Nonlinear Samespots software (see below) as the reference gel for the entire set of gels, and this gel was then fixed in buffer (10% methanol, 7% acetic acid in ddH20), and directly stained with SyproRuby stain (INVITROGEN™, Carlsbad, Calif.), and destained in buffer. SyproRuby is an ionic dye that typically labels proteins with multiple fluors, including a Sypro-stained gel in the analysis ensures that the maximum number of proteins can be detected and quantified. The destained gels was scanned at 555/580 nm (ex/em). The exposure time for both dyes was adjusted to achieve a value of ~55,000-63,000 pixel intensity (16-bit saturation) from the most intense protein spots on the gel.

Measurement of Relative Spot Intensities

The 2D gel images were analyzed using Progenesis/SameSpots software (Nonlinear Dynamics, Ltd. Newcastle Upon Tyne, UK). The reference gel was selected according to quality and number of spots. Once "landmarks" were defined the program performed automatic spot detection on all images. This strategy ensures that spot numbers and outlines were identical across all gels in the experiment, eliminating problems with unmatched spots (13;14). Spot volumes were normalized using a software-calculated bias value assuming that the great majority of spot volumes did not change in abundance.

Protein Identification

Selected 2DE spots were picked robotically, trypsin-digested, and peptide masses identified by MALDI TOF/TOF (AB Sciex 4800, Applied Biosystems, Foster City, Calif.). Following MALDI MS analysis, MALDI MS/MS was performed on several (5-10) abundant ions fromea ch sample spot. For MS/MS data, 2,000 laser shots were acquired and averaged from each sample spot.

Applied Biosystems GPS EXPLORER™ software was used in conjunction with MASCOT to search the respective protein database using both MS and MS/MS spectral data for protein identification. Protein match probabilities were determined using expectation values and/or MASCOT protein scores. Protein identification was performed using a Bayesian algorithm (15) where matches were indicated by expectation score, an estimate of the number of matches that would be expected in that database if the matches were completely random. Confirmation of the protein identification was performed by LC-MS/MS (Orbitrap Velos, ThermoFinnegan, San Jose, Calif.).

Statistical Analysis

Statistical comparisons were performed using SAS®, version 9.1.3 (SAS, Inc., Cary, N.C.) and PASW Statistics 17.0, Release 17.0.2 (SPSS, Inc., Chicago, Ill.).

Multivariate Analysis of Variance (MANOVA)

The multivariate analysis of variance model is a popular statistical model used to determine whether significant mean differences exist among disease and gender groups. One advantage of MANOVA is that the correlation structure is taken into consideration between each cytokine. The Wilk's' lambda statistics as a MANOVA-based score were used to analyze data, when there is more than one dependent variable (SAS 9.2 PROC GLM).

Multivariate Adaptive Regression Splines (MARS)

MARS is a non-parametric regression method that uses piecewise linear spline functions (basis functions) as predictors. The basis functions are combinations of independent variables, and so this method allows detection of feature interactions and performs well with complex data structures (16). MARS uses a two-stage process for constructing the optimal classification model. The first half of the process involves creating an overly large model by adding basis functions that represent either single variable transformations or multivariate interaction terms. The model becomes more flexible and complex as additional basis functions are added. The process is complete when a user-specified number of basis functions have been added. In the second stage, MARS deletes basis functions in order, starting with the basis function that contributes the least to the model until an optimum model is reached. By allowing the model to take on many forms as well as interactions, MARS can reliably track the very complex data structures that are often present in high-dimensional data. By doing so, MARS effectively reveals important data patterns and relationships that other models often struggle to detect. Cross-validation techniques were used within MARS to avoid over-fitting the classification model. In this example, Log-transformed cytokine and normalized spot intensities from 2DE were modeled using 10-fold cross validation and a maximum of 126 functions (Salford Systems, Inc).

Generalized Additive Models (GAM)

GAMs were estimated by a backfitting algorithm within a Newton-Raphson technique. SAS® 9.2 PROC GAM and STATISTICA 8.0 to fit the GAM fittings with binary logit link function that provided multiple types of smoothers with automatic selection of smoothing parameters.

Results

Cytokine Analyses

Plasma proteins were isolated from subjects obtained during initial clinical visit. Focused proteomics analyses were performed using bead-based immunoplex to measure cytokines that have been associated with DHF in previous studies (17;18). These measurements included IL-6, IL-10, IFN-γ, IP-10, MIP-1α, TNFα, IL-2, vascular endothelial growth factor (VEGF), and TNF-related apoptosis-induced ligand (TRAIL). Analysis of the plasma concentrations of the cytokines indicated that their distributions were highly skewed. Despite logarithmic transformation of the data, the data remained non-normally distributed. As a result, the cytokines were compared between the two outcomes using the Wilcoxon rank-sum test. A permutation test was used to derive p-values based on the violation of normal assumption. Only two cytokines retained significance between DF and DHF, IL-6 ($p=0.002$) and IL-10 ($p<0.001$) (FIG. 1A, B). For both cytokines, the median value of the log 2-transformed concentration was greater in DHF than that of DF subjects.

Differences between cytokines were analyzed as a function of gender using two-factor ANOVA. For IL-6 and IL-10, MIP-1α, and TRAIL, gender is found significant for diagnosis (DF vs. DHF) (Table II). To correct for correlated cytokines, a MANOVA test was applied to the overall data. In this analysis, both gender (p=0.0165) and diagnosis (p<0.0001) had significant Wilks-Lamba p values. Together, these analyses indicate that gender is an important confounding variable in the cytokine response to dengue infection.

TABLE II

Two-way ANOVA for detection of interactions between gender and disease.

| Cytokine | Source | Type III Sum of Squares | Df | Mean Square | F | Sig. |
| --- | --- | --- | --- | --- | --- | --- |
| IL-6 | Disease | 0.637 | 1 | 0.637 | 11.034 | 0.002 |
|  | Gender | 0.335 | 1 | 0.335 | 5.795 | 0.020 |
|  | Disease*Gender | 0.032 | 1 | 0.032 | 0.559 | 0.459 |
|  | Error | 2.715 | 47 | 0.058 |  |  |
|  | Total | 3.557 | 50 |  |  |  |
| IL-10 | Disease | 4.643 | 1 | 4.643 | 28.675 | 0.000 |
|  | Gender | 0.667 | 1 | 0.667 | 4.182 | 0.046 |
|  | Disease*Gender | 0.231 | 1 | 0.231 | 1.428 | 0.238 |
|  | Error | 7.610 | 47 | 0.162 |  |  |
|  | Total | 12.531 | 50 |  |  |  |

Biofluid Analysis Platform (BAP)

The BAP, a discovery-based sample prefractionation method with 2-DE using saturation fluorescence labeling, was applied to more comprehensively identify proteins associated with the development of DHF. The BAP combines a high recovery Superdex S-75 size-exclusion chromatography (SEC) of plasma with electronically triggered fraction collection to create protein and peptide pools for subsequent separation and analysis. An important feature of the BAP is the utilization of de-ionized urea to initially dissociate protein/peptide complexes in the plasma prior to SEC. The initial denaturation of the plasma prior to rapid SEC fractionation avoids the pitfall of peptide binding to high abundance plasma carrier proteins (27; 28). Moreover, SEC is a non-adsorptive, high recovery prefractionation approach that achieves 95-100% recovery of the input protein. Downstream of SEC, antibody depletion results in significant increase in proteome coverage, enhancing detection of low abundance proteins (31). Finally, our development of a quantitative saturation fluorescence labeling produces 2DE to identify differentially expressed proteins (32).

One hundred and six serum samples, representing acute and convalescent samples from 53 subjects were analyzed by BAP. Four hundred and nineteen spots were mapped and the normalized spot intensities were compared. For the purposes of biomarker panel development, normalized spot intensities were compared between DF and DHF in the acute samples. From this analysis, 34 spots met statistical cut-off criteria (p<0.05, t-test).

Multivariate Adaptive Regression Spline (MARS)-Based Modeling for Predictors of DHF Because the proteomic quantifications violated normal distributions, and included outliers, nonparametric modeling methods were evaluated. MARS is a robust, nonparametric, piecewise linear approach that establishes relationships within small intervals of independent variables, detects feature interactions and is generally resistant to the effects of outlier influence (20). MARS can estimate complex nonlinear relationships by a series of spline functions of the predictor variables. Regression splines seek to find thresholds and breaks in relationships between variables and are very well suited for identifying changes in the behavior of individuals or processes over time. Some of the advantages of MARS are that it can model predictor variable of many forms, whether continuous or categorical, and can tolerate large numbers of input predictor variables and can easily deal with missing values. As a nonparametric approach, MARS does not make any underlying assumptions about the distribution of the predictor variables of interest.

To identify features important in DHF, gender, logarithm-transformed cytokine expression values (IL-6 and IL-10), and 34 2DE protein spots were modeled using 10-fold cross-validation and a maximum of 126 basis functions, schematically diagrammed in FIG. 2. The optimal model was selected on the basis of the lowest cross-validation error, which included 1 cytokine (IL-10) and 7 protein spots including: tropomyosin, complement 4A, immunoglobulin V, fibrinogen, and three isoforms of albumin. The proteins that corresponded to each predictive spot were identified by LC-MS/MS analysis (Table III). The confidence for identification of each protein was high, given as the expectation score. The location of the 7 proteins spots on 2DE and the effect of disease on their abundance is shown in FIG. 3. The 2DE analysis provided additional information not accessible by shotgun-based mass spectrometry. For example, the albumin isoforms were distinct isoforms of albumin as indicated by their unique isoelectric points (Table IV, FIG. 3). Moreover, two of the albumin isoforms, represented as spots 505 and 507, were much larger than native albumin, suggesting that they were cross-linked proteins.

TABLE III

Protein identification of MARS features. Shown are the protein identifications for the 2-DE proteins identified that contribute to the MARS predictive classifier for DHF.

| No. | Protein name | GI Accession no. | UniProt accession no. | Gel spot no. | pI | MW (Da) | MS ID expectation value |
| --- | --- | --- | --- | --- | --- | --- | --- |
| 1 | C4A | 239740686 | XP_002343974 | 156 | 8.18 | 71 | 5.00E−10 |
| 2 | Albumin* | 168988718 | P02768 | 206 | 6.28 | 52 | 2.51E−57 |
| 3 | Fibrinogen | 237823914 | P02671 | 276 | 7.35 | 40 | 9.98E−38 |
| 4 | Tropomyosin | 10441386 | AAG17014 | 332 | 5.08 | 29 | 1.58E−41 |
| 5 | Immunoglobulin gamma V | 567146 | AAA52924 | 371 | 8.81 | 24 | 7.92E−04 |
| 6 | Albumin* | 168988718 | P02768 | 506 | 6.19 | 263 | 5.00E−47 |
| 7 | Albumin* | 168988718 | P02768 | 507 | 6.23 | 263 | 6.29E−32 |

A comparison of the normalized spot intensities for the 7 discriminant proteins were plotted by the outcome of dengue disease (FIG. 6). Similar to the cytokine analysis, although the proteins differ by median value, the analysis of the distribution of normalized and logarithm-transformed protein concentrations, derived either from quantitative bead-based ELISA or normalized spot intensities from the saturation fluorescence labeled 2DE analysis, were highly overlapping (FIGS. 1, 6), suggesting that, if used as single measurement, they would not be informative or robust biomarkers. Any singular protein would have poor ability to discriminate between disease types. Moreover, the protein concentrations were not normally distributed and therefore demand analysis by non-parametric methods.

The optimal MARS model is represented by a linear combination of 9 basis functions, where each basis function is a range over which the individual protein's concentration contributes to the classification basis functions, whose values are shown in Table IV (A). Also of note, the basis functions are composed of single biomarker, indicating that interactions between the biomarkers do not contribute significantly to the discrimination. Using combined BAP-nonparametric MARS modeling approach, our most accurate model for the prediction of DHF was based on IL-10, C4A, fibrinogen, trypomoyosin, immunoglobulin, and several albumin isoforms. This model was able to accurately predict DHF in 100% of the cases, and evaluation of the sensitivity-specificity relationship by ROC analysis indicated a very good fit of the model to our data. The model diagnostics using GAM further provide support that nonlinear approaches were appropriate to associate disease state with protein expression patterns. Prediction success is shown in Table IV (B)

TABLE IV(A)

MARS Basis Functions. Shown are the basis functions (BF) for the MARS model for dengue hemorrhagic fever.

| $B_m$ | Definition | $a_m$ | Variable descriptor |
|---|---|---|---|
| BF1 | $(IL-10 - 1.15)_+$ | 5.83E-03 | IL-10 |
| BF3 | $(20873 - Fibrinogen)_+$ | 5.42E-05 | Fibrinogen |
| BF5 | $(437613 - Albumin)_+$ | 1.39E-06 | Albumin*1 |
| BF6 | $(C4A - 385932)_+$ | -4.90E-06 | Complement 4A |
| BF8 | $(C4A - 256959)_+$ | 3.25E-06 | Complement 4A |
| BF11 | $(469259 - Albumin)_+$ | 2.48E-06 | Albumin*2 |
| BF17 | $(122218 - TPM4)_+$ | 5.27E-06 | TPM4 |
| BF19 | $(Immunoglobulin\ gamma - 57130)_+$ | -1.35E-06 | Immunoglobulin gamma-chain, V region |
| BF23 | $(657432 - Albumin)_+$ | -9.97E-07 | Albumin*3 |

Bm, each individual basis function,
$a_m$, coefficient of the basis function.
$(y)_+ = \max(0, y)$.
*Variable isoforms likely due to post-translational modification and/or proteolysis.

TABLE IV(B)

Confusion matrix for MARS classifier of DHF. For each disease (class), the prediction success of the MARS classifier is shown.

| | | Prediction | |
|---|---|---|---|
| Class | Total | DF (n = 38) | DHF (n = 13) |
| DF | 38 | 38 | 0 |
| DHF | 13 | 0 | 13 |
| Total | 51 | correct = 100% | correct = 100% |

To determine which of these biomarkers contribute the most information to the model, variable importance was assessed. Variable importance is a relative indicator (from 0-100%) for the contribution of each variable to the overall performance of the model (FIG. 3). The variable importance computed for the top three proteins was IL-10 (100%), with Albumin*1 (50%) followed by fibrinogen (40%).

Example 2: DHF MARS Detection Model Validation

The performance of the MARS predictor of DHF was assessed using several approaches. First, the overall accuracy of the model on the data set was analyzed by minimizing classification error using cross-validation. The model accuracy produced 100% accuracy for both DHF and DF classification (Table IV(B)). Another evaluation of the model performance is seen by analysis of the area under the Receiver Operating Characteristic (ROC) curve (AUC), where Sensitivity vs. one-Specificity was plotted. In the ROC analysis, a diagonal line starting at zero indicated that the output was a random guess, whereas an ideal classifier with a high true positive rate and low false positive rate will curve positively and strongly towards the upper left quadrant of the plot (21). The AUC is equivalent to the probability that two cases, one chosen at random from each group, are correctly ordered by the classifier (22). In the DHF MARS model, an AUC of 1.000 is seen (FIG. 4), indicating a highly accurate classifier on the data set.

Post-Hoc Generalized Additive Model (GAM) Analysis

To confirm that a nonparametric method was the most appropriate modeling approach for these discriminant proteins, the predictive variables were subjected to a GAM analysis. GAMs are data-driven modeling approaches used to identify nonlinear relationships between predictive features and clinical outcome when there are a large number of independent variables (23;24). Inspection of the residual plots for tropomyosin, complement 4, and albumin isoforms *1-*4 indicate that these variables do not satisfy classical assumptions for the use of linear modeling (FIG. 6). By contrast, IL-10 and immunoglobulin gamma approximate a global linear relationship. This analysis indicates that modeling approaches that assume global linear relationships, such as logistic regression, are not generally suited to relate information in proteomics measurements to clinical phenotypes or outcomes.

Previous work has shown that soluble mediators, including IL-2, IL-4, IL-6, IL-10, IL-13 and IFN-γ are found in plasma in increased concentrations in patients with severe dengue infections (17). In a prospective study of a single serotype outbreak in Cuba, IL-10 was observed to be higher in individuals with secondary dengue infections (18). It is also noted that dengue loading into monocytes in vitro resulted in enhanced IL-6 and IL-10 production (35). The identification of IL-10 in this study as increased in DHF is a partial validation of inventive modeling.

Previous work has shown that immunological responses to vaccines are significantly affected by gender (36). Interestingly, the two-factor ANOVA disclosed previously is the first observation to our knowledge that links gender to cytokine response in acute dengue fever infections. This gender effect confounds the statistical analysis of mixed gender population studies. Recognition of this finding will be important to guide the design of subsequent biomarker verification studies.

In the analysis of clinical parameters measured upon initial entry into the study showed that the platelet concentration is significantly reduced in subjects with DHF vs DF. Thrombocytopenia is a well established feature of DHF, responsible in part for increased tendency for cutaneous hemorrhages. The origin of thrombocytopenia in DHF is thought to be the consequence of both bone marrow depression and accelerated antibody-mediated platelet sequestration by the liver (37). Despite its statistical association with DHF, platelet counts do not contribute as strongly to an overall classifier of DHF as do circulating IL-10, immunoglobulin gamma, and albumin isoforms. In addition to the tropism of dengue virus for monocytes and dendritic cells, severe dengue infections also involve viral-induced liver damage (38). In this regard, increases in liver transaminases (AST) as well as decreases in albumin concentration have been observed (39). These phenomena probably represent leakage of hepatocyte cytoplasm and impairment in hepatic synthetic capacity, respectively. In this study, 2DE fractionation of plasma proteins provided an additional dimension of information not accessible by clinical assays. For example, the alternative migration of albumin isoforms (albumin *1-*3, FIG. 2), differing in molecular weight and isoelectric points, would not be detectable by mass spectrometry or by clinical assays. Although albumin is a target for nonenzymatic glycosylation and ischemia-induced oxidation, the biochemical processes underlying these changes in albumin in dengue infections are presently unknown.

Fibrinogen is an important predictor in the MARS model, with reduced and its concentration as a result of DHF (FIG. 6). Fibrinogen is a major component of the classical coagulation cascade. In this regard, coagulation defects, similar to mild disseminated intravascular coagulation, are seen in DHF. In fact, isotopic studies indicated a rapid turnover of fibrinogen (40), thereby explaining its reduction in patients with DHF measured by our analysis. Previous work using a 2D differential fluorescence gel approach comparing individuals with dengue fever versus normal controls, identified reduced fibrinogen expression (41). However, from the design of this study, the use of fibrinogen to differentiate DF from DHF could not be assessed.

In summary, using nonparametric modeling methods for developing predictive classifiers using a high resolution focused and discovery-based approach, a highly accurate classifier of DHF based on IL-10, fibrinogen, C4A, immunoglobulin gamma, tropomyosin, and three isoforms of albumin were found. Most of these biomarkers can be linked to the biological processes underlying that of DHF, including cytokine storm, capillary leakage, hepatic injury, and antibody consumption, suggesting that these predictors may have biological relevance. All references cited in this application are herein incorporated by reference.

Example 3: Linear Model for DHF Prediction

Although the nonparametric modeling method of example 2 has achieved great accuracy in identifying dengue infected patients who are at risk for developing DHF, the clinical application of this biomarker panel will require development of accurate methods for quantification of modified plasma proteins that can be adapted and disseminated into clinical laboratories, especially in those endemic areas. Therefore, it is important to have an early DHF detection model that is based solely on the combinations of clinical and accessible laboratory tests.

Sample Collection and Preparation

An active surveillance for dengue diseases study was conducted in Maracay, Venezuela. Subjects are enrolled if presented with a new fever equal to or greater than 38° C. accompanied by two or more of the signs and symptoms consistent with dengue virus infection including: myalgia, arthralgia, leucopenia, rash, headache, lymphoadenopathy, nausea, vomiting, positive tourniquet test, thrombocytopenia, or hepatomegaly. On the day of presentation, a blood sample was collected for dengue virus RT-PCR confirmation and clinical chemistries. Viral RNA was prepared from 140 µl sera using QIAamp Viral RNA Mini Kits following the manufacturer's instructions (QIAGENR® Inc., Valencia, Calif.). Nested dengue virus RT-PCR was performed on serum samples for virus detection as described. Individuals with confirmed dengue infections were monitored for clinical outcome, and DF and DHF cases were scored following WHO case definitions.

Multiplex Bead-Based Cytokine Measurements

Plasma samples were analyzed for the concentrations of 9 human cytokines, including IL-6, IL-10, IFN-γ, IP-10, MIP-1α, TNFα, IL-2, vascular endothelial growth factor (VEGF), and TNF-related apoptosis-induced ligand (TRAIL). For each analyte, a standard curve was generated using recombinant proteins to estimate protein concentration in the unknown sample. For the purposes of modeling, the cytokine values were log 2-transformed to approximate a normal distribution.

Bayesian Variable Selection for Generalized Additive Models

To select the models of predictors between smoothing nonlinear terms, and linear effects, Bayesian variable selection were performed in GAM (implemented in the R package spikeSlabGAM). Best subsets logistic regression model building used SAS®, version 9.1.3 (SAS, Inc., Cary, N.C.). GAMs were estimated by a backfitting algorithm within a Newton-Raphson technique. SAS 9.2 PROC GAM and STATISTICA 8.0 to fit the GAM fittings with binary logit link function that provided multiple types of smoothers with automatic selection of smoothing parameters.

Classification and Regression Tree Modeling

CART decision tree model building was performed with CART, Salford Systems, San Diego, Calif.). CART is an iterative classification method for variable selection and predicting categorical response variables that uses a splitting rule to identify a predictive variable and a cutoff that best breaks the population into homogenous classes. The splitting rule was entropy using equal priors (equal likelihood) for the DHF and DF classes. The model was tested using 10-fold cross validation.

Multivariate Logistic Regression Modeling for DHF

Within the study population, a set of 11 parameters were selected, including gender, clinical signs, laboratory measurements (lymphocyte/neutrophil/platelet counts, hemoglobin concentration, red blood cell count) and cytokine concentration (IL-10, IL-6, TRAIL). Because the underlying data structures for the clinical parameters dictates the selection of an appropriate modeling approach, we analyzed the contributions of parametric (linear) or nonparametric (spline) features using bayesian variable selection. This method produces a hierarchy of structured model selections for parametric and nonparametric relationships to the outcome for each feature. The posterior probabilities for the linear and spline components are shown in Table V. The linear component of the log 2-transformed IL-10 (LIL10) had a marginal inclusion probability [P*(gamma=1)] of greater than 0.5, indicating LIL10 could be considered as a parametric feature. Similarly, the linear component of gender [P*(gamma=1)>0.25], and the lymphocyte count [P*(gamma=1)>0.25] all have high posterior probabilities that they are related to the disease outcome. We noted that our previous studies found IL-10 to be statistically significant by disease (p<0.001) that had an interaction component with gender and was the major variable contributing to the proteomics biomarker panel (3).

TABLE V

Marginal posterior inclusion probability and term importance.

| Coefficients | P(gamma = 1) | Pi | dimension |
|---|---|---|---|
| linear(LIL10) | 0.751 | 0.773 | 1** |
| spline(LIL10) | 0.001 | 0.000 | 8 |
| fct(Sex) | 0.392 | 0.070 | 1* |
| linear(Platelets) | 0.136 | 0.059 | 1 |
| spline(Platelets) | 0.053 | 0.001 | 8 |
| linear(Lymphocytes) | 0.458 | 0.098 | 1* |
| spline(Lymphocytes) | 0.011 | 0.000 | 8 |

Shown are the posterior model probabilities from the MCMC 8000 samples from 8 chains, each ran 5000 iterations after a burn-in of 500.
*P(gamma = 1) > .25;
**P(gamma = 1) > .5.

The Bayesian feature selection approach suggested that linear components of the feature set were related to outcome. Features were analyzed by chi-square ($\chi 2$) analysis, an approach that assumes the features have a linear relationship with outcome. The rank-ordered list of features are shown in Table VI. Here, plasma IL-10 ($\chi 2=17$), platelet concentration ($\chi 2=14.2$) and lymphocyte count ($\chi 2=5$) features with large $\chi 2$ values.

TABLE VI

Rank ordered list of features informative for DHF.

| Variable | Chi-Square |
|---|---|
| IL-10 | 17.269 |
| Platelet Count | 14.209 |
| IL-6 | 6.602 |
| Diarrhea | 6.234 |
| Days of Fever | 5.938 |
| Hemoglobin | 5.210 |
| Lymphocytes | 5.056 |
| Neutrophils | 4.194 |
| Red blood cell count | 3.600 |
| Sex | 2.862 |
| TRAIL | 2.4631 |

| Effect | Point Estimate | 95% Wald Confidence limits | |
|---|---|---|---|
| Platelet Count | 0.964 | 0.934 | 0.994 |
| Lymphocytes | 0.890 | 0.802 | 0.989 |
| IL-10 | 5.944 | 1.172 | 30.136 |

Logistic Regression Modeling of DHF

Because the feature reduction suggested that the clinical and laboratory data were linearly related with outcome, a logistic regression modeling approach is therefore employed for the prediction of DHF. Model building was performed using best subsets selection starting with the entire feature list (Table VI). Of the input variables, initial platelet and lymphocyte concentrations and log 2-transformed IL-10 were retained in the model. The odds ratio and 95% confidence limits are shown (Table VII). Increases in IL-10 concentrations were associated with increased probability of DHF, whereas decreases in platelet and lymphocyte counts were associated with increased probability of DHF.

TABLE VII

Odds ratios for DHF logistic regression model.

| Effect | Point Estimate | 95% Wald Confidence limits | |
|---|---|---|---|
| Platelet Count | 0.964 | 0.934 | 0.994 |
| Lymphocytes | 0.890 | 0.802 | 0.989 |
| IL-10 | 5.944 | 1.172 | 30.136 |

Example 4: DHF Logistic Regression Model Validation

The Receiver Operating Characteristic (ROC) curve (AUC), where sensitivity vs. 1-specificity was plotted was used to evaluate the model performance. In the ROC analysis, a diagonal line starting at zero indicating that the output was a random guess, whereas an ideal classifier with a high true positive rate and low false positive rate will curve positively and strongly towards the upper left quadrant of the plot. The AUC is equivalent to the probability that two cases, one chosen at random from each group, are correctly ordered by the classifier. In the DHF Linear Regression model, an AUC of 9.615 was obtained (FIG. 8). Overall these findings indicated that excellent performance of the logistic regression model on this data set.

To confirm the logistic regression model, we conducted a Bayesian-independent GAM analysis separately modeling the parametric and nonparametric components of the features. The $\chi 2$ statistic in the linear component analysis of deviance was statistically significant (Table VIII), where the parametric (linear) components for LIL10, platelets, and lymphocytes were highly significant with p-values of 0.037, 0.022, and 0.035, respectively, equivalent to the results produced by logistic regression. This analysis also indicates that the nonlinear "smoothing" components of the IL10, platelets, and lymphocytes are not significant at the level alpha of 0.05 with the GAM fit (using df=3). Additionally, since p-value=0.8950 for Hosmer and Lemeshow Goodness-of-fit test, we conclude that the logistic regression response function is appropriate. Together these data further validate the parametric modeling approach using linear regression.

TABLE IV

Smoothing model analysis of deviance tests.

| Parameters | df | Chi-square | Pr > chisq |
|---|---|---|---|
| linear(LL10) | 1 | 3.46 | 0.071* |
| linear(Platelets) | 1 | 6 | 0.019* |
| Linear(Lymphocytes) | 1 | 3.725 | 0.06* |
| Spline(LL10) | 2 | 5.577 | 0.062 |
| Spline(Platelets) | 2 | 2.562 | 0.278 |
| Spline(Lymphocytes) | 2 | 3.341 | 0.188 | df, degrees of freedom.

Finally, we examined the distribution of residuals for the logistic regression model. Residual plots of LR assume additivity of the predictors are useful for examining if individual points are not well fit or influence model performance. We used the deviance residual, partial residual, DFFITS and DFBETAS to identify influential observations (FIG. 2). Two outlier/influential data points were identified. LR model building including or excluding these observations produced no significant difference of p-values of IL-10, Lymphocytes, and Platelets indicating that the model is robust.

CART Decision Tree

To aid in the clinical application of the logistic regression model, we sought to represent the three predictive features as a decision tree. CART is a machine learning tool that seeks to identify the best cut-off for each analyte that produces the most accurate classification of DHF or DF. The features that best separates the DHF from DF is selected first, and the process is repeated until all the subjects are classified. Ten-fold cross validation, a process dividing the data into random training and test sets, is performed to estimate classification error and to prune the tree to prevent over-fitting. Performing 10 trials using 10-fold cross validation resulted in the best model with an average accuracy of 84.6% for DHF and 84% for DF (FIG. 10). Here, four terminal nodes are produced by the CART classifier. Twenty five of the DHF cases can be predicted on the basis of platelet count alone; another 6 are identified on the basis of low LIL10 and low lymphocyte counts. The AUC for the test data was 0.87.

As discussed previously, IL-10 is an immuno-suppressive cytokine secreted by primary monocytes in response to Dengue virus infection mediated by ADE. The detection of IL-10 in our samples from acutely infected patients is consistent with this observation in vitro. An reduced platelet concentrations were also identified as being associated with DHF in this study. Thrombocytopenia is a well-established feature of DHF, responsible in part for increased tendency for cutaneous hemorrhages. Cell mediated immunity is an important mechanism protective immunity to Dengue infections. Although circulating lymphocyte counts are not reflective if cellular activation, our study indicates that patients who develop DHF have reduced lymphocyte concentrations at presentation. A prospective study of 91 subjects with dengue infection in Taiwan described that a lower percentage of "typical" lymphocytes were observed in subjects with severe dengue infection. Our findings here indicate that lymphocyte counts are also reduced in DHF, but lymphocyte concentrations are not as informative as IL-10 cytokine concentrations and platelet counts with disease outcome.

CART trees are readily human interpretable as simple decisions that result in a classification. Although CART model here does not quite perform as well as the logistic regression model (in terms of AUC). Nevertheless, the CART analysis suggests that the subjects with Dengue infections have specific characteristics. Those with high platelet counts are very likely to have uncomplicated DF, whereas those with low platelet counts and high IL-10 are likely to have DHF. The group with low platelet counts; low IL-10 and low lymphocytes are equally represented by DF and DHF outcomes. In summary, parametric modeling approaches using accessible clinical data (IL-10, platelets and lymphocyte counts) of patients acutely presenting with RT-PCR confirmed Dengue infections shows promise for the early detection of DHF. These predictive models will require further validation on independent study populations.

REFERENCES

1. Martina, B. E. E., Koraka, P., and Osterhaus, A. D. M. E. 2009. Dengue Virus Pathogenesis: an Integrated View. Clin. Microbiol. Rev. 22:564-581.

2. Pinheiro, F. P., and Corber, S. J. 1997. Global situation of dengue and dengue haemorrhagic fever, and its emergence in the Americas. World Health Stat. Q. 50:161-169.

3. Guzman, M. G., Kouri, G., Bravo, J., Valdes, L., Vazquez, S., and Halstead, S. B. 2002. Effect of age on outcome of secondary dengue 2 infections. Int. J Infect. Dis 6:118-124.

4. Guzman, M. G., and Kouri, G. 2003. Dengue and dengue hemorrhagic fever in the Americas: lessons and challenges. J Clin. Virol. 27:1-13.

5. Graham, R. R., Juffrie, M., Tan, R., Hayes, C. G., Laksono, I., Ma'roef,C., Erlin, Sutaryo, Porter, K. R., and Halstead, S. B. 1999. A prospective seroepidemiologic study on dengue in children four to nine years of age in Yogyakarta, Indonesia I. studies in 1995-1996. Am J Trop Med Hyg 61:412-419.

6. Thomas, L., Verlaeten, O., Cabie, A., Kaidomar, S., Moravie, V., Martial, J., Najioullah, F., Plumelle, Y., Fonteau, C., Dussart, P. et al 2008. Influence of the dengue serotype, previous dengue infection, and plasma viral load on clinical presentation and outcome during a dengue-2 and dengue-4 co-epidemic. Am J Trop Med Hyg 78:990-998.

7. Ranjit, S., Kissoon, N., and Jayakumar, I. 2005. Aggressive management of dengue shock syndrome may decrease mortality rate: A suggested protocol*. Pediatric Critical Care Medicine 6.

8. World Health Organization (WHO) 1997. Dengue haemorrhagic fever: diagnosis, treatment, and control. World Health Organization.

9. Jamaluddin, M., Wiktorowicz, J. E., Soman, K. V., Boldogh, I., Forbus, J., Spratt, H., Garofalo, R. P., and Brasier, A. R. 2010. Role of Peroxiredoxin-1 and -4 in Protection of RSV-induced Cysteinyl-oxidation of Nuclear Cytoskeletal Proteins. J Virol 84:9533-9545.

10. Pretzer, E. P., and Wiktorowicz, J. E. 2007. Saturation fluorescence labeling of proteins for proteomic analyses. Anal. Biochem. in press.

11. Turck, C. W., Falick, A. M., Kowalek, J. A., Lane, W. S., Lilley, K. S., Phinney, B. S., Weintraub, S. T., Wikowska, H. E., and Yates, N. A. 2006. ABRF-PRG06: Relative protein quantification. In Association of Biomolecular Resource Facilities. Long Beach, Calif.

12. Miseta, A., and Csutora, P. 2000. Relationship between the occurrence of cysteine in proteins and the complexity of organisms. Molecular Biology of Evolution 17:1232-1239.

13. Dowsey, A. W., Morris, J. S., Gutstein, H. B., and Yang, G. Z. 2010. Informatics and statistics for analyzing 2-d gel electrophoresis images. Methods Mol. Biol 604:239-255.

14. Karp, N. A., Feret, R., Rubtsov, D. V., and Lilley, K. S. 2008. Comparison of DIGE and post-stained gel electrophoresis with both traditional and SameSpots analysis for quantitative proteomics. Proteomics 8:948-960.

15. Zhang, W., and Chait, B. T. 2000. ProFound: An Expert System for Protein Identification Using Mass Spectrometric Peptide Mapping Information. Anal. Chem. 72:2482-2489.

16. Friedman, J. H. 1991. Multivariate Adaptive Regression Splines Annals of Statistics 19:1-67.

17. Bozza, F., Cruz, O., Zagne, S., Azeredo, E., Nogueira, R., Assis, E., Bozza, P., and Kubelka, C. 2008. Multiplex cytokine profile from dengue patients: MIP-1beta and IFN-gamma as predictive factors for severity. BMC Infectious Diseases 8:86.

18. Perez, A. B., Garcia, G., Sierra, B., Alvarez, M., Vasquez, S., Cabrera, M. V., Rodriguez, R., Rosario, D., Martinez, E., Denny, T. et al 2004. IL-10 levels in Dengue patients: some findings from the exceptional epidemiological conditions in Cuba. J Med Virol 73:230-234.

19. Tyagarajan, K., Pretzer, E. P., and Wiktorowicz, J. E. 2003. Thiol-reactive dyes for fluorescence labeling of proteomic samples. Electrophoresis 24:2348-2358.

20. Cook, N. R., Zee, R. Y. L., and Ridker, P. M. 2005. Tree and spline based association of gene-gene interaction models for ischemic stroke. Statistics in Medicine 23:1439-1453.

21. Fawcett, T. 2006. An introduction to ROC analysis. Pattern Recognition Letters 27:861-874.

22. Hanley, J. A., and McNeil, B. J. 1982. The meaning and use of the area under a receiver operating characteristic curve. Radiology 143:29-36.

23. Austin, P. C. 2007. A comparison of regression trees, logistic regression, generalized additive models, and multivariate adaptive regression splines for predicting AMI mortality. Stat. Med 26:2937-2957.

24. Hastie, T., and Tibshirani, R. 1995. Generalized additive models for medical research. Stat. Methods Med Res 4:187-196.

25. Anderson, N. L., and Anderson, N. G. 2002. The Human Plasma Proteome: History, Character, and Diagnostic Prospects. Mol Cell Proteomics 1:845-867.

26. Rifai, N., and Gerszten, R. E. 2006. Biomarker Discovery and Validation. Clinical Chemistry 52:1635-1637.

27. Gundry, R. L., Fu, Q., Jelinek, C. A., Van Eyk, J. E., and Cotter, R. J. 2007. Investigation of an albumin-enriched fraction of human serum and its albuminome. Proteomics Clin. Appl. 1:73-88.

28. Seferovic, M. D., Krughkov, V., Pinto, D., Han, V. K., and Gupta, M. B. 2008. Quantitative 2-D gel electrophoresis-based expression proteomics of albumin and IgG immunodepleted plasma. J Chromatogr. B Analyt. Technol. Biomed. Life Sci. 865:147-152.

29. Villanueva, J., Philip, J., Chaparro, C. A., Li, Y., Toledo-Crow, R., DeNoyer, L., Fleisher, M., Robbins, R. J., and Tempst, P. 2005. Correcting common errors in identifying cancer-specific serum peptide signatures. J Proteome Res. 4:1060-1072.

30. Villanueva, J., Nazarian, A., Lawlor, K., Yi, S. S., Robbins, R. J., and Tempst, P. 2008. A sequence-specific exopeptidase activity test (SSEAT) for "functional" biomarker discovery. Mol. Cell Proteomics 7:509-518.

31. Tu, C., Rudnick, P. A., Martinez, M. Y., Cheek, K. L., Stein, S. E., Slebos, R. J. C., and Liebler, D. C. 2010. Depletion of Abundant Plasma Proteins and Limitations of Plasma Proteomics. J. Proteome Res. 9:4982-4991.

32. Pretzer, E. P., and Wiktorowicz, J. E. 2008. Saturation fluorescence labeling of proteins for proteomic analyses. Anal. Biochem. 374:250-262.

33. Endy, T. P., Nisalak, A., Chunsuttitwat, S., Vaughn, D. W., Green, S., Ennis, F. A., Rothman, A. L., and Libraty, D. H. 2004. Relationship of Preexisting Dengue Virus (DV) Neutralizing Antibody Levels to Viremia and Severity of Disease in a Prospective Cohort Study of DV Infection in Thailand. J Infect Dis 189:990-1000.

34. Green, S., and Rothman, A. 2006. Immunopathological mechanisms in dengue and dengue hemorrhagic fever. Curr. Opin. Infect. Dis 19:429-436.

35. Chareonsirisuthigul, T., Kalayanarooj, S., and Ubol, S. 2007. Dengue virus (DENV) antibody-dependent enhancement of infection upregulates the production of anti-inflammatory cytokines, but suppresses anti-DENV free radical and pro-inflammatory cytokine production, in THP-1 cells. J. Gen. Virol. 88:365-375.

36. Klein, S. L., Jedlicka, A., and Pekosz, A. 2010. The Xs and Y of immune responses to viral vaccines. Lancet Infect. Dis. 10:338-349 (Abstr.)

37. Mitrakul, C., Poshyachinda, M., Futrakul, P., Sangkawibha, N., and Ahandrik, S. 1977. Hemostatic and Platelet Kinetic Studies in Dengue Hemorrhagic Fever. Am J Trop Med Hyg 26:975-984.

38. Seneviratne, S. L., Malavige, G. N., and de Silva, H. J. 2006. Pathogenesis of liver involvement during dengue viral infections. Trans. R. Soc. Trop Med Hyg 100:608-614.

39. Villar-Centeno, L. A., Diaz-Quijano, F. A., and Martinez-Vega, R. A. 2008. Biochemical Alterations as Markers of Dengue Hemorrhagic Fever. Am J Trop Med Hyg 78:370-374.

40. Srichaikul, T., Nimmanitaya, S., Artchararit, N., Siriasawakul, T., and Sungpeuk, P. 1977. Fibrinogen Metabolism and Disseminated Intravascular Coagulation in Dengue Hemorrhagic Fever. Am J Trop Med Hyg 26:525-532.

41. Albuquerque, L. M., Trugilho, M. R. O., Chapeaurouge, A., Jurgilas, P.ü.B., Bozza, P.ü.T., Bozza, F. A., Perales, J., and Neves-Ferreira, A. G. C. 2009. Two-Dimensional Difference Gel Electrophoresis (DiGE) Analysis of Plasmas from Dengue Fever Patients. J. Proteome Res. 8:5431-5441.

42. Avirutnan, P., Punyadee, N., Noisakran, S., Komoltri, C., Thiemmeca, S., Auethavornanan, K., Jairungsri, A., Kanlaya, R., Tangthawornchaikul, N., Puttikhunt, C. et al 2006. Vascular leakage in severe dengue virus infections: a potential role for the nonstructural viral protein NS1 and complement. J Infect. Dis 193:1078-1088.

43. Thayan, R., Huat, T. L., See, L. L., Tan, C. P., Khairullah, N. S., Yusof, R., and Devi, S. 2009. The use of two-dimension electrophoresis to identify serum biomarkers from patients with dengue haemorrhagic fever. Trans. R. Soc. Trop Med Hyg 103:413-419.

44. Pieper, R., Gatlin, C. L., Makusky, A. J., Russo, P. S., Schatz, C., Miller, S. S., Su, Q., McGrath, A. M., Estock, M. A., Parmar, P. P. et al 2003. The human serum proteome: Display of nearly 3700 chromatographically separated protein spots on two-dimensional electrophoresis gels and identification of 325 distinct proteins. Proteomics 3:1345-1364.

45. San Martin J L, Brathwaite O, Zambrano B, et al. Th epidemiology of dengue in the Americas over the last three decades: a worrisome reality. Am J Trop Med Hyg 2010; 82:128-35.

What is claimed is:

1. A sample fractionation method for albumin biomarker identification comprising:
   (a) fractionating a sample derived from blood by size exclusion chromatography, wherein the sample has protein/peptide complexes dissociated by denaturation and the sample is spiked with a labeled protein of about 200 amino acid residues for differentiating protein and peptide pools;
   (b) collecting a (i) protein pool comprising the fractions preceding the end of the labeled protein peak, and (ii) a peptide pool comprising the fractions after the end of the labeled protein peak and before the free dye peak;
   (c) incubating the collected protein pool to allow for renaturation of the collected proteins in the protein pool;
   (d) depleting the protein pool by exposing the protein pool to an antibody depletion column and collecting column flow through to produce a depleted sample;
   (e) labeling the depleted sample with an uncharged thiol reactive label forming a saturated fluorescence labeled sample;

(f) conducting two dimensional (2D) gel electrophoresis on the saturated fluorescence labeled sample, producing a 2D gel;

(g) imaging the 2D gel and identifying a protein(s) of interest, wherein the protein of interest is an albumin isoform; and (h) conducting mass spectrometry analysis of the protein(s) of interest.

2. The method of claim 1, wherein the size exclusion chromatography uses a size exclusion column having a separation range between molecular weights of 3,000 to 70,000 daltons.

3. The method of claim 1, wherein the spiked labeled protein is a labeled thaumatin.

4. The method of claim 1, wherein the antibody depletion column is an IgY antibody depletion column.

5. The method of claim 1, wherein the thiol reactive label is bodipy FL-maleimide.

\* \* \* \* \*